(12) United States Patent
Shoseyov et al.

(10) Patent No.: US 9,109,047 B2
(45) Date of Patent: Aug. 18, 2015

(54) HIGH MOLECULAR ORDERED FIBRILAR STRUCTURES, METHOD FOR THEIR PREPARATION AND USES THEREOF

(75) Inventors: Oded Shoseyov, Karmei Yosef (IL); Shaul Lapidot, Kibbutz Tzora (IL); Sigal Meirovitch, Tel Aviv (IL)

(73) Assignee: Yissum Research Development Company of the Hebrew University of Jerusalem Ltd, Jerusalem (IL)

( * ) Notice: Subject to any disclaimer, the term of this patent is extended or adjusted under 35 U.S.C. 154(b) by 0 days.

(21) Appl. No.: 13/981,330

(22) PCT Filed: Feb. 2, 2012

(86) PCT No.: PCT/IL2012/000058
§ 371 (c)(1),
(2), (4) Date: Jul. 24, 2013

(87) PCT Pub. No.: WO2012/104840
PCT Pub. Date: Aug. 9, 2012

(65) Prior Publication Data
US 2014/0031526 A1    Jan. 30, 2014

Related U.S. Application Data

(60) Provisional application No. 61/439,120, filed on Feb. 3, 2011.

(51) Int. Cl.
| | |
|---|---|
| *C07K 14/78* | (2006.01) |
| *C07K 14/435* | (2006.01) |
| *D01F 4/00* | (2006.01) |
| *D01F 9/00* | (2006.01) |

(52) U.S. Cl.
CPC ............ *C07K 14/78* (2013.01); *C07K 14/43518* (2013.01); *C07K 14/43536* (2013.01); *C07K 14/43586* (2013.01); *D01F 4/00* (2013.01); *D01F 9/00* (2013.01); *C07K 2319/20* (2013.01)

(58) Field of Classification Search
None
See application file for complete search history.

(56) References Cited

U.S. PATENT DOCUMENTS

2010/0317588 A1    12/2010   Shoseyov et al.

FOREIGN PATENT DOCUMENTS

| WO | WO 01/34091 A2 * | 5/2001 |
| WO | WO 2006076711 | 7/2006 |
| WO | WO 2009069123 | 6/2009 |

OTHER PUBLICATIONS

Xu et al. (2008) "*Characterization of a cellulose binding domain from Clostridium cellulovorans endoglucanase-xylanase D and its use as a fusion partner for soluble protein expression in Escherichia coli,*" J. Biotechnol. 135:319-25.
Xu et al. (1995) "*Solution Structure of a Cellulose-Binding Domain from Cellulomonas fimi by Nuclear Magnetic Resonance Spectroscopy,*" Biochemistry 34:6993-7009.
Gatesy et al. (2001) "*Extreme Diversity, Conservation, and Convergence of Spider Silk Fibroin Sequences,*" Science 291:2603-2605.
Fahnestock et al. (1997) "*Production of synthetic spider dragline silk protein in Pichia pastoris,*" Appl. Microbiol. Biotechnol. 47:33-39.
Fahnestock et al. (1997) "*Synthetic spider dragline silk proteins and their production in Escherichia coli,*" Appl. Microbiol. Biotechnol. 47:23-32.
Sceller et al. (2001) "*Production of spider silk proteins in tobacco and potato,*" Nature biotechnology 19:573-577.
Székely et al. (2010) "*Solution X-ray Scattering Form Factors of Supramolecular Self-Assembled Structures,*" Langmuir 26:13110-29.
Ben-Nun et al. (2010) "*X+: a comprehensive computationally accelerated structure analysis tool for solution X-ray scattering from supramolecular self-assemblies,*" J. Appl. Cryst. 43:1522-1531.
UniProtKB/Swiss-Prot: P19837 (Spidroin 1), 1991.
Genebank AAC38957 (Spidroin 1), 2007.
Genebank ABR68858 (Spidroin 2), 2007.
Genebank AAT75317 (Spidroin 2), 2010.
UniProtKB/Swiss-Prot: P46804 (Spidroin 2), 1995.
Genebank AAL83649, 2002.
Genebank AAA27839, 1993.
NCBI Reference Sequence: NP001106733, 2013.
NCBI Reference Sequence: NP001037488, 2013.
Genebank CAA35180, 1991.
Seq. 32 from WO 2009069123, 2009.
Seq. 34 from WO 2009069123, 2009.
Meirovitch (2007) Symposium T: The Nature of Design-Utilizing Biology's Portfolio (XP002519708).
Shoseyov (2008) Symposium DD: From Biological Materials to Biomimetic Material Synthesis (XP002546728).
Qin et al. (2010) "*Expression, cross-linking and characterization of recombinant chitin binding resilin,*" (XP031664991).
Levy et al. (2004) "*Engineering a bifunctional starch-cellulose cross-bridge protein,*" Biomaterials 25:1841-1849.
Bini et al. (2006) "*RGD-Functionalized Bioengineered Spider Dragline Silk Biomaterial,*" Biomacromolecules 7:3139-3145.
International Search Report (PCT/IL2012/000058; 4 pages), 2012.

* cited by examiner

*Primary Examiner* — Suzanne M Noakes
(74) *Attorney, Agent, or Firm* — William C. Schrot; AuerbachSchrot LLC

(57) ABSTRACT

The present invention relates to methods for generation of high molecular ordered fibrilar structures. More particularly, the method of the invention utilizes CBD's (cellulose binding domain) ability to form dimers for directing ordered assembly of fibrous proteins such as silk proteins into super-molecular fibrilar structures. The invention further provides fibrilar structures such as fibers and articles comprising said fibrilar structures.

6 Claims, 12 Drawing Sheets

```
ggctaacaattcccctctagaaataattttgtttaactttaagaaggagatatacatatg
                                                            M
caccatcatcatcatcattcttctggtctggtgccacgcggttctggtatgaaagaaacc
H  H  H  H  H  H  S  S  G  L  V  P  R  G  S  G  M  K  E  T
gctgctgctaaattcgaacgccagcacatggacagcccagatctgggtaccgacgacgac
 A  A  A  K  F  E  R  Q  H  M  D  S  P  D  L  G  T  D  D  D
gacaaggccatggctagcggtgttggcggtctgggtggccagggtgcaggtgctgctgcg
 D  K  A  M  A  S  G  E  G  G  L  G  G  Q  G  A  G  A  A  A
gcagcaggcggtgctggccaaggtgcctacggtggcctgggttctcagggtactagcggt
 A  A  G  A  G  Q  G  G  Y  G  G  L  G  S  Q  G  T  S  G
cgtggcggtctgggtggccagggtgcaggtgctgctgcggcagcaggcggtgctggca
 R  G  G  L  G  G  Q  G  A  G  A  A  A  A  G  G  A  G  Q
ggtggctacggtggcctgggttctcagggtactagcggtcgtggcggtctgggtggccag
 G  G  Y  G  G  L  G  S  Q  G  T  S  G  R  G  G  L  G  G  Q
ggtgcaggtgctgctgcggcagcaggcggtgctggccaaggtgcctacggtggcctgggt
 G  A  G  A  A  A  A  G  G  A  G  Q  G  G  Y  G  G  L  G
tctcagggtactagcggtcgtggcggtctgggtggccagggtgcaggtgctgctgcggca
 S  Q  G  T  S  G  R  G  G  L  G  G  Q  G  A  G  A  A  A
gcaggcggtgctggccaaggtgcctacggtggcctgggttctcagggtactagcggtcgt
 A  G  G  A  G  Q  G  G  Y  G  G  L  G  S  Q  G  T  S  G  R
ggcggtctgggtggccagggtgcaggtgctgctgcggcagcaggcggtgctggccaaggt
 G  G  L  G  G  Q  G  A  G  A  A  A  A  G  G  A  G  Q  G
ggctacggtggcctgggttctcagggtactagcggtcgtggcggtctgggtggccagggt
 G  Y  G  G  L  G  S  Q  G  T  S  G  R  G  G  L  G  G  Q  G
gcaggtgctgctgcggcagcaggcggtgctggccaaggtgcctacggtggcctgggttct
 A  G  A  A  A  A  G  G  A  G  Q  G  G  Y  G  G  L  G  S
cagggtactagcggtcgtggcggtctgggtggccagggtgcaggtgctgctgcggcagca
 Q  G  T  S  G  R  G  G  L  G  G  Q  G  A  G  A  A  A  A
ggcggtgctggccaaggtgcctacggtggcctgggttctcagggtactagcggtcgtggc
 G  G  A  G  Q  G  G  Y  G  G  L  G  S  Q  G  T  S  G  R
ggtctgggtggccagggtgcaggtgctgctgcggcagcaggcggtgctggccaaggtggc
 G  L  G  G  Q  G  A  G  A  A  A  A  G  G  A  G  Q  G
tacggtggcctgggttctcagggtactagcggtcgtggcggtctgggtggccagggtgca
 Y  G  G  L  G  S  Q  G  T  S  G  R  G  G  L  G  G  Q  G  A
ggtgctgctgcggcagcaggcggtgctggccaaggtggctacggtggcctgggttctcag
 G  A  A  A  A  G  G  A  G  Q  G  G  Y  G  G  L  G  S  Q
ggtactagcggtcgtggcggtctgggtggccagggtgcaggtgctgctgcggcagcaggc
 G  T  S  G  R  G  G  L  G  G  Q  G  A  G  A  A  A  A  G
ggtgctggccaaggtggctacggtggcctgggttctcagggtactagcggtcgtggcggt
 G  A  G  Q  G  G  Y  G  G  L  G  S  Q  G  T  S  G  R  G  G
ctgggtggccagggtgcaggtgctgctgcggcagcaggcggtgctggccaaggtggctac
 L  G  G  Q  G  A  G  A  A  A  A  G  G  A  G  Q  G  G  Y
ggtggcctgggttctcagggtactagcggtcgtggcggtctgggtggccagggtgcaggt
 G  G  L  G  S  Q  G  T  S  G  R  G  G  L  G  G  Q  G
gctgctgcggcagcaggcggtgctggccaaggtggctacggtggcctgggttctcagggt
 A  A  A  A  G  G  A  G  Q  G  G  Y  G  G  L  G  S  Q  G
actagcggtcgtggcggtctgggtggccagggtgcaggtgctgctgcggcagcaggcggt
 T  S  G  R  G  G  L  G  G  Q  G  A  G  A  A  A  A  G
gctggccaaggtggctacggtggcctgggttctcagggtactagcggtcgtggcggtctg
 A  G  Q  G  G  Y  G  G  L  G  S  Q  G  T  S  G  R  G  G  L
ggtggccagggtgcaggtgctgctgcggcagcaggcggtgctggccaaggtggctacggt
 G  G  Q  G  A  G  A  A  A  A  G  G  A  G  Q  G  G  Y  G
ggcctgggttctcagggtactagcggtcgtggcggtctgggtggccagggtgcaggtgct
 G  L  G  S  Q  G  T  S  G  R  G  G  L  G  G  Q  G  A  G  A
gctgcggcagcaggcggtgctggccaaggtggctacggtggcctgggttctcagggtact
 A  A  A  A  G  G  A  G  Q  G  G  Y  G  G  L  G  S  Q  G  T
agtggatccgccggctagagcggccgcactcgagcaccaccaccaccaccactgagat
 S  G  S  A  R  A  A  A  L  E  H  H  H  H  H  H  *
```

Fig. 1

```
ccatgtcagttgaattctacaactctaacaaatcagcacaaacaaactcaattacaccaata
  M  S  V  E  F  Y  N  S  N  K  S  A  Q  T  N  S  I  T  P  I
atcaaaattactaacacatctgacagtgatttaaatttaaatgacgtaaaagttagatat
  I  K  I  T  N  T  S  D  S  D  L  N  L  N  D  V  K  V  R  Y
tattacacaagtgatggtacacaaggacaaactttctggtgtgaccatgctggtgcatta
  Y  Y  T  S  D  G  T  Q  G  Q  T  F  W  C  D  H  A  G  A  L
ttaggaaatagctatgttgataacactagcaaagtgacagcaaacttcgttaaagaaaca
  L  G  N  S  Y  V  D  N  T  S  K  V  T  A  N  F  V  K  E  T
gcaagcccaacatcaacctatgatacatatgttgaatttggatttgcaagcggacgagct
  A  S  P  T  S  T  Y  D  T  Y  V  E  F  G  F  A  S  G  R  A
actcttaaaaaaggacaatttataactattcaaggaagaataacaaaatcagactggtca
  T  L  K  K  G  Q  F  I  T  I  Q  G  R  I  T  K  S  D  W  S
aactacactcaaacaaatgactattcatttgatgcaagtagttcaacaccagttgtaaat
  N  Y  T  Q  T  N  D  Y  S  F  D  A  S  S  S  T  P  V  V  N
ccaaaagttacaggatatataggtggagctaaagtacttggtacagcaccaggtccagat
  P  K  V  T  G  Y  I  G  G  A  K  V  L  G  T  A  P  G  P  D
gtaccatcttcaataattaatcctacttctgcaacatttgatcccggtaccatggctagc
  V  P  S  S  I  I  N  P  T  S  A  T  F  D  P  G  T  M  A  S
atgactggtggacagcaaatgggtcggatcc
  M  T  G  G  Q  Q  M  G  R  I
```

Fig. 2

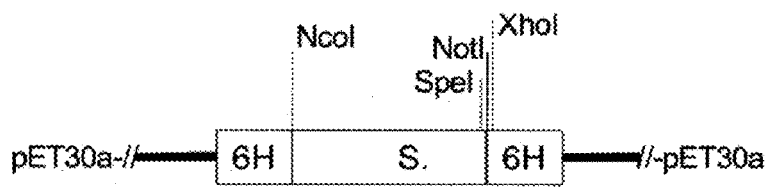

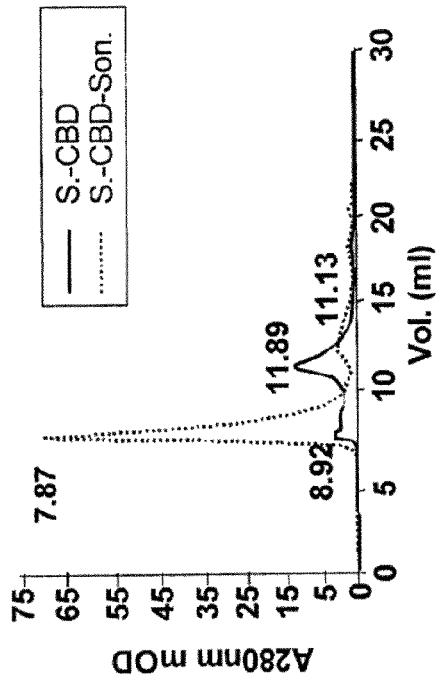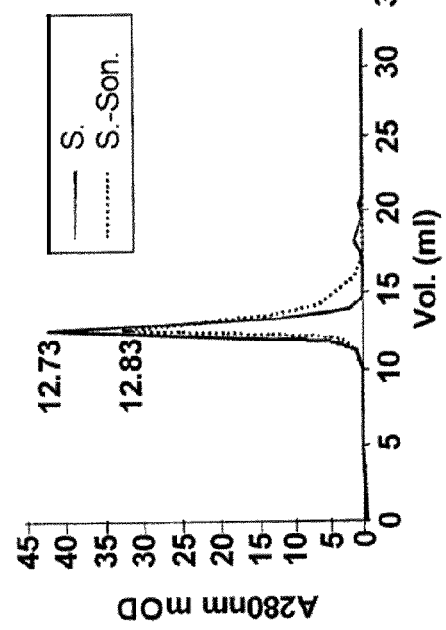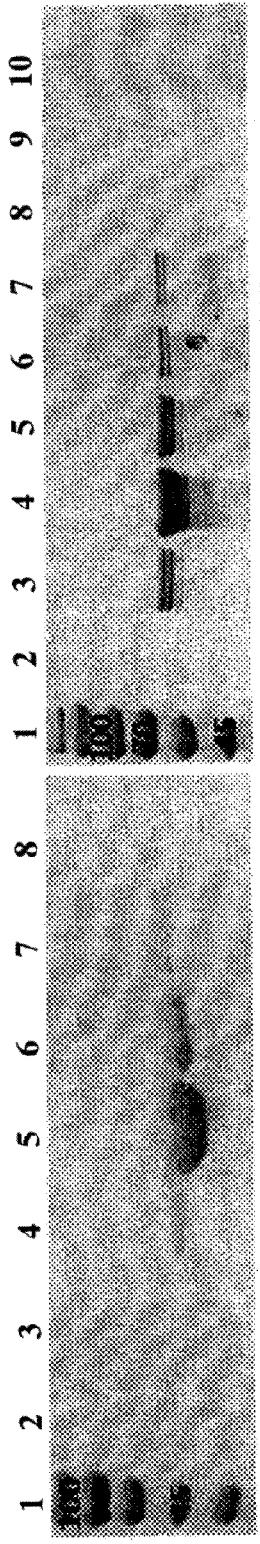

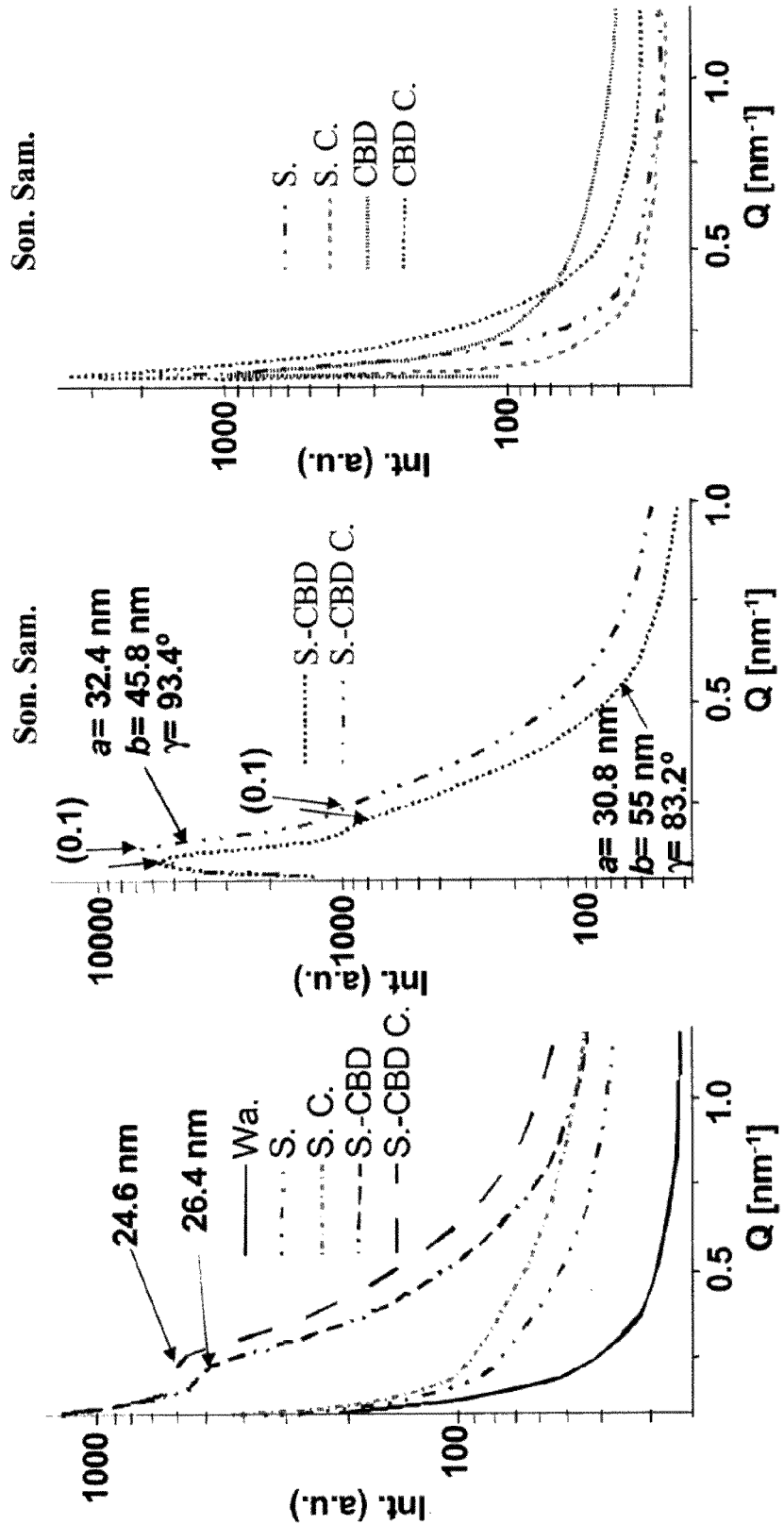

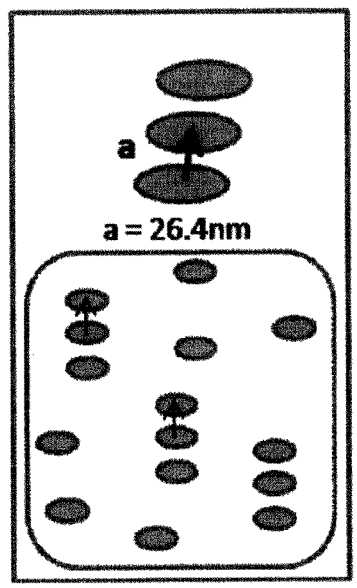
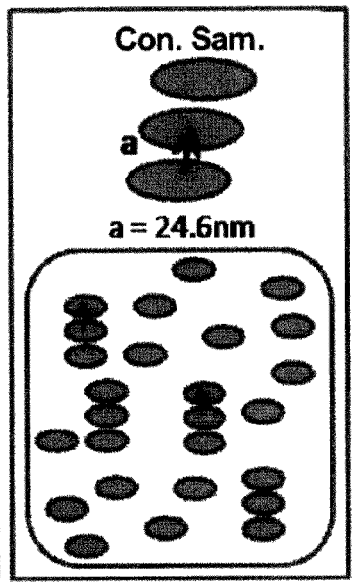
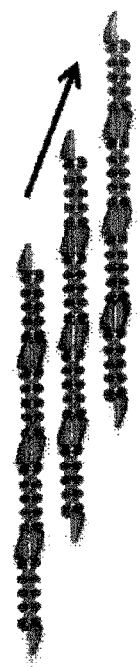
Fig. 12A     Fig. 12B     Fig. 12C
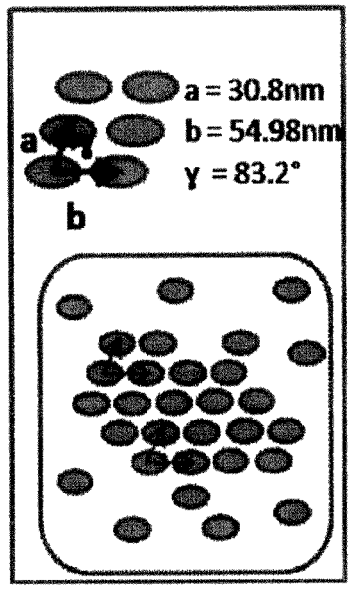
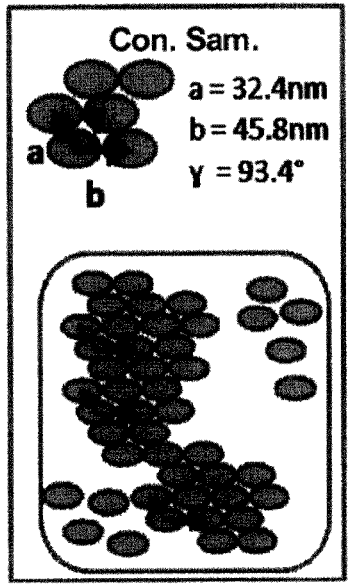
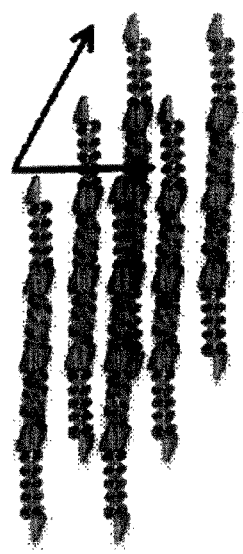
Fig. 12D     Fig. 12E     Fig. 12F

SEQUENCE LISTING

<160> NUMBER OF SEQ ID NOS: 16

<210> SEQ ID NO 1
<211> LENGTH: 1740
<212> TYPE: DNA
<213> ORGANISM: Nephila clavipes

<400> SEQUENCE: 1

```
ggctaacaat tcccctctag aaataatttt gtttaacttt aagaaggaga tatacatatg      60
caccatcatc atcatcattc ttctggtctg gtgccacgcg gttctggtat gaaagaaacc     120
gctgctgcta aattcgaacg ccagcacatg gacagcccag atctgggtac cgacgacgac     180
gacaaggcca tggctagcgg tcgtggcggt ctgggtggcc agggtgcagg tgctgctgcg     240
gcagcaggcg gtgctggcca aggtggctac ggtggcctgg gttctcaggg tactagcggt     300
cgtggcggtc tgggtggcca gggtgcaggt gctgctgcgg cagcaggcgg tgctggccaa     360
ggtggctacg gtggcctggg ttctcagggt actagcggtc gtggcggtct gggtggccag     420
ggtgcaggtg ctgctgcggc agcaggcggt gctggccaag gtggctacgg tggcctgggt     480
tctcagggta ctagcggtcg tggcggtctg ggtggccagg gtgcaggtgc tgctgcgca      540 gcaggcggtg ctggccaagg tggctacggt ggcctgggtt ctcagggtac tagcggtcgt     600
```

-continued

```
ggcggtctgg gtggccaggg tgcaggtgct gctgcggcag caggcggtgc tggccaaggt    660
ggctacggtg gcctgggttc tcagggtact agcggtcgtg gcggtctggg tggccagggt    720
gcaggtgctg ctgcggcagc aggcggtgct ggccaaggtg gctacggtgg cctgggttct    780
cagggtacta gcggtcgtgg cggtctgggt ggccagggtg caggtgctgc tgcggcagca    840
ggcggtgctg gccaaggtgg ctacggtggc ctgggttctc agggtactag cggtcgtggc    900
ggtctgggtg gccagggtgc aggtgctgct gcggcagcag gcggtgctgg ccaaggtggc    960
tacggtggcc tgggttctca gggtactagc ggtcgtggcg gtctgggtgg ccagggtgca   1020
ggtgctgctg cggcagcagg cggtgctggc caaggtggct acggtggcct gggttctcag   1080
ggtactagcg gtcgtggcgg tctgggtggc agggtgcag tgctgctgc ggcagcaggc   1140
ggtgctggcc aaggtggcta cggtggcctg ggttctcagg gtactagcgg tcgtggcggt   1200
ctgggtggcc agggtgcagg tgctgctgcg gcagcaggcg gtgctggcca aggtggctac   1260
ggtggcctgg gttctcaggg tactagcggt cgtggcggtc tgggtggcca gggtgcaggt   1320
gctgctgcgc agcaggcgg tgctggccaa ggtggctacg gtggcctggg ttctcagggt   1380
actagcggtc gtggcggtct gggtggccag ggtgcaggtg ctgctgcggc agcaggcggt   1440
gctggccaag gtgctacgg tggcctgggt tctcagggta ctagcggtcg tggcggtctg   1500
ggtggccagg gtgcaggtgc tgctgcggca gcaggcggtgc tggccaagg tggctacggt   1560
ggcctgggtt ctcagggtac tagcggtcgt ggcggtctgg gtggccaggg tgcaggtgct   1620
gctgcggcag caggcggtgc tggccaaggt ggctacggtg gcctgggttc tcagggtact   1680
agtggatccg cccgggctag agcggccgca ctcgagcacc accaccacca ccactgagat   1740
```

<210> SEQ ID NO 2
<211> LENGTH: 559
<212> TYPE: PRT
<213> ORGANISM: Nephila clavipes

<400> SEQUENCE: 2

Met His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Ala Met Ala Ser Gly
        35                  40                  45

Arg Gly Gly Leu Gly Gly Gln Gly Ala Gly Ala Ala Ala Ala Gly
    50                  55                  60

Gly Ala Gly Gln Gly Gly Tyr Gly Gly Leu Gly Ser Gln Gly Thr Ser
65                  70                  75                  80

Gly Arg Gly Gly Leu Gly Gly Gln Gly Ala Gly Ala Ala Ala Ala
                85                  90                  95

Gly Gly Ala Gly Gln Gly Gly Tyr Gly Gly Leu Gly Ser Gln Gly Thr
            100                 105                 110

Ser Gly Arg Gly Gly Leu Gly Gly Gln Gly Ala Gly Ala Ala Ala
        115                 120                 125

Ala Gly Gly Ala Gly Gln Gly Gly Tyr Gly Gly Leu Gly Ser Gln Gly
    130                 135                 140

Thr Ser Gly Arg Gly Gly Leu Gly Gly Gln Gly Ala Gly Ala Ala Ala
145                 150                 155                 160

Ala Ala Gly Gly Ala Gly Gln Gly Gly Tyr Gly Gly Leu Gly Ser Gln
                165                 170                 175

```
Gly Thr Ser Gly Arg Gly Gly Leu Gly Gly Gln Gly Ala Gly Ala Ala
            180                 185                 190

Ala Ala Ala Gly Gly Ala Gly Gln Gly Gly Tyr Gly Gly Leu Gly Ser
        195                 200                 205

Gln Gly Thr Ser Gly Arg Gly Gly Leu Gly Gly Gln Gly Ala Gly Ala
        210                 215                 220

Ala Ala Ala Ala Gly Gly Ala Gly Gln Gly Gly Tyr Gly Gly Leu Gly
225                 230                 235                 240

Ser Gln Gly Thr Ser Gly Arg Gly Gly Leu Gly Gly Gln Gly Ala Gly
                245                 250                 255

Ala Ala Ala Ala Ala Gly Gly Ala Gly Gln Gly Gly Tyr Gly Gly Leu
            260                 265                 270

Gly Ser Gln Gly Thr Ser Gly Arg Gly Gly Leu Gly Gly Gln Gly Ala
        275                 280                 285

Gly Ala Ala Ala Ala Gly Gly Ala Gly Gln Gly Gly Tyr Gly Gly
        290                 295                 300

Leu Gly Ser Gln Gly Thr Ser Gly Arg Gly Gly Leu Gly Gly Gln Gly
305                 310                 315                 320

Ala Gly Ala Ala Ala Ala Gly Gly Ala Gly Gln Gly Gly Tyr Gly
                325                 330                 335

Gly Leu Gly Ser Gln Gly Thr Ser Gly Arg Gly Gly Leu Gly Gly Gln
            340                 345                 350

Gly Ala Gly Ala Ala Ala Ala Gly Gly Ala Gly Gln Gly Gly Tyr
        355                 360                 365

Gly Gly Leu Gly Ser Gln Gly Thr Ser Gly Arg Gly Gly Leu Gly Gly
        370                 375                 380

Gln Gly Ala Gly Ala Ala Ala Ala Gly Gly Ala Gly Gln Gly Gly
385                 390                 395                 400

Tyr Gly Gly Leu Gly Ser Gln Gly Thr Ser Gly Arg Gly Gly Leu Gly
                405                 410                 415

Gly Gln Gly Ala Gly Ala Ala Ala Ala Gly Gly Ala Gly Gln Gly
            420                 425                 430

Gly Tyr Gly Gly Leu Gly Ser Gln Gly Thr Ser Gly Arg Gly Gly Leu
        435                 440                 445

Gly Gly Gln Gly Ala Gly Ala Ala Ala Ala Gly Gly Ala Gly Gln
        450                 455                 460

Gly Gly Tyr Gly Gly Leu Gly Ser Gln Gly Thr Ser Gly Arg Gly Gly
465                 470                 475                 480

Leu Gly Gly Gln Gly Ala Gly Ala Ala Ala Ala Gly Gly Ala Gly
                485                 490                 495

Gln Gly Gly Tyr Gly Gly Leu Gly Ser Gln Gly Thr Ser Gly Arg Gly
            500                 505                 510

Gly Leu Gly Gly Gln Gly Ala Gly Ala Ala Ala Ala Gly Gly Ala
        515                 520                 525

Gly Gln Gly Gly Tyr Gly Gly Leu Gly Ser Gln Gly Thr Ser Gly Ser
        530                 535                 540

Ala Arg Ala Arg Ala Ala Ala Leu Glu His His His His His His
545                 550                 555
```

<210> SEQ ID NO 3
<211> LENGTH: 573
<212> TYPE: DNA
<213> ORGANISM: Clostridium cellulovorans

<400> SEQUENCE: 3

```
ccatgtcagt tgaattctac aactctaaca aatcagcaca acaaactca attacaccaa    60
taatcaaaat tactaacaca tctgacagtg atttaaattt aaatgacgta aaagttagat   120
attattacac aagtgatggt acacaaggac aaactttctg gtgtgaccat gctggtgcat   180
tattaggaaa tagctatgtt gataacacta gcaaagtgac agcaaacttc gttaaagaaa   240
cagcaagccc aacatcaacc tatgatacat atgttgaatt tggatttgca agcggacgag   300
ctactcttaa aaaggacaa tttataacta ttcaaggaag aataacaaaa tcagactggt   360
caaactcac tcaaacaaat gactattcat ttgatgcaag tagttcaaca ccagttgtaa   420
atccaaaagt tacaggatat ataggtggag ctaaagtact tggtacagca ccaggtccag   480
atgtaccatc ttcaataatt aatcctactt ctgcaacatt tgatcccggt accatggcta   540
gcatgactgg tggacagcaa atgggtcgga tcc                                573
```

<210> SEQ ID NO 4
<211> LENGTH: 190
<212> TYPE: PRT
<213> ORGANISM: Clostridium cellulovorans

<400> SEQUENCE: 4

```
Met Ser Val Glu Phe Tyr Asn Ser Asn Lys Ser Ala Gln Thr Asn Ser
 1               5                  10                  15
Ile Thr Pro Ile Ile Lys Ile Thr Asn Thr Ser Asp Ser Asp Leu Asn
            20                  25                  30
Leu Asn Asp Val Lys Val Arg Tyr Tyr Tyr Thr Ser Asp Gly Thr Gln
        35                  40                  45
Gly Gln Thr Phe Trp Cys Asp His Ala Gly Ala Leu Leu Gly Asn Ser
    50                  55                  60
Tyr Val Asp Asn Thr Ser Lys Val Thr Ala Asn Phe Val Lys Glu Thr
65                  70                  75                  80
Ala Ser Pro Thr Ser Thr Tyr Asp Thr Tyr Val Glu Phe Gly Phe Ala
                85                  90                  95
Ser Gly Arg Ala Thr Leu Lys Lys Gly Gln Phe Ile Thr Ile Gln Gly
            100                 105                 110
Arg Ile Thr Lys Ser Asp Trp Ser Asn Tyr Thr Gln Thr Asn Asp Tyr
        115                 120                 125
Ser Phe Asp Ala Ser Ser Ser Thr Pro Val Val Asn Pro Lys Val Thr
    130                 135                 140
Gly Tyr Ile Gly Gly Ala Lys Val Leu Gly Thr Ala Pro Gly Pro Asp
145                 150                 155                 160
Val Pro Ser Ser Ile Ile Asn Pro Thr Ser Ala Thr Phe Asp Pro Gly
                165                 170                 175
Thr Met Ala Ser Met Thr Gly Gly Gln Gln Met Gly Arg Ile
            180                 185                 190
```

<210> SEQ ID NO 5
<211> LENGTH: 2280
<212> TYPE: DNA
<213> ORGANISM: Artificial Sequence
<220> FEATURE:
<223> OTHER INFORMATION: DNA sequence encoding the Silk 6H-15-mer-CBD
      fusion protein

```
<400> SEQUENCE: 5
ggctaacaat tcccctctag aaataatttt gtttaacttt aagaaggaga tatacatatg      60
caccatcatc atcatcattc ttctggtctg gtgccacgcg gttctggtat gaaagaaacc     120
gctgctgcta aattcgaacg ccagcacatg gacagcccag atctgggtac cgacgacgac     180
gacaaggcca tggctagcgg tcgtggcggt ctgggtggcc agggtgcagg tgctgctgcg     240
gcagcaggcg gtgctggcca aggtggctac ggtggcctgg gttctcaggg tactagcggt     300
cgtggcggtc tgggtggcca gggtgcaggt gctgctgcgg cagcaggcgg tgctggccaa     360
ggtggctacg gtggcctggg ttctcagggt actagcggtc gtggcggtct gggtggccag     420
ggtgcaggtg ctgctgcggc agcaggcggt gctggccaag gtggctacgg tggcctgggt     480
tctcagggta ctagcggtcg tggcggtctg gtggccaggt gtgcaggtgc tgctgcggca     540
gcaggcggtg ctggccaagg tggctacggt ggcctgggtt ctcagggtac tagcggtcgt     600
ggcggtctgg gtggccaggg tgcaggtgct gctgcggcag caggcggtgc tggccaaggt     660
ggctacggtg gcctgggttc tcagggtact agcggtcgtg gcggtctggg tggccagggt     720
gcaggtgctg ctgcggcagc aggcggtgct ggccaaggtg gctacggtgg cctgggttct     780
cagggtacta gcggtcgtgg cggtctgggt ggccagggtg caggtgctgc tgcggcagca     840
ggcggtgctg gccaaggtgg ctacggtggc ctgggttctc agggtactag cggtcgtggc     900
ggtctgggtg gccagggtgc aggtgctgct gcggcagcag gcggtgctgg ccaaggtggc     960
tacggtggcc tgggttctca gggtactagc ggtcgtggcg gtctgggtgg ccagggtgca    1020
ggtgctgctg cggcagcagg cggtgctggc caaggtggct acggtggcct gggttctcag    1080
ggtactagcg gtcgtggcgg tctgggtggc cagggtgcag gtgctgctgc ggcagcaggc    1140
ggtgctggcc aaggtggcta cggtggcctg ggttctcagg gtactagcgg tcgtggcggt    1200
ctgggtggcc agggtgcagg tgctgctgcg gcagcaggcg gtgctggcca aggtggctac    1260
ggtggcctgg gttctcaggg tactagcggt cgtggcggtc tgggtggcca gggtgcaggt    1320
gctgctgcgg cagcaggcgg tgctggccaa ggtggctacg gtggcctggg ttctcagggt    1380
actagcggtc gtggcggtct gggtggccag ggtgcaggtg ctgctgcggc agcaggcggt    1440
gctggccaag gtggctacgg tggcctgggt tctcagggta ctagcggtcg tggcggtctg    1500
ggtgccaggg tgcaggtgc tgctgcggca gcaggcggtg ctggccaagg tggctacggt    1560
ggcctgggtt ctcagggtac tagcggtcgt ggcggtctgg gtggccaggg tgcaggtgct    1620
gctgcggcag caggcggtgc tggccaaggt ggctacggtg gcctgggttc tcagggtact    1680 agtatgcag cgacatcatc aatgtcagtt gaattttaca actctaacaa agcagcacaa    1740
acaaactcaa ttacaccaat aatcaaaatt actaacacag ctgacagtga tttaaattta    1800
aatgacgtaa aagttagata ttattacaca agtgatggta cacaaggaca aactttctgg    1860
ggtgatcatg ctggtgcatt attaggaaat agctatgttg ataacactgg caaagtgaca    1920
gcaaacttcg ttaaagaaac agcaagccca acatcaacct atgatacata tgttgaattt    1980
ggatttgcaa gcggagcagc tactcttaaa aaaggacaat ttataactat tcaaggaaga    2040
ataacaaaat cagactggtc aaactacgct cagacaaatg actattcatt tgatgcaagt    2100
agttcaacac cagttgtaaa tccaaaagtt acaggatata taggtggagc taaagtactt    2160
ggtacagcac caggtccaga tgtaccatct tcaataatta atcctacttc tgcaacattt    2220
gatctcgagc accaccacca ccactgctga gatccggctg ctaacaaagc ccgaaaggaa    2280
```

<210> SEQ ID NO 6
<211> LENGTH: 730
<212> TYPE: PRT
<213> ORGANISM: Artificial Sequence
<220> FEATURE:
<223> OTHER INFORMATION: Amino acid sequence of the Silk 6H-15-mer-CBD fusion protein

<400> SEQUENCE: 6

```
Met His His His His His Ser Ser Gly Leu Val Pro Arg Gly Ser
1               5                   10                  15

Gly Met Lys Glu Thr Ala Ala Lys Phe Glu Arg Gln His Met Asp
            20                  25                  30

Ser Pro Asp Leu Gly Thr Asp Asp Asp Lys Ala Met Ala Ser Gly
        35                  40                  45

Arg Gly Gly Leu Gly Gly Gln Gly Ala Gly Ala Ala Ala Ala Gly
    50                  55                  60

Gly Ala Gly Gln Gly Gly Tyr Gly Gly Leu Gly Ser Gln Gly Thr Ser
65                  70                  75                  80

Gly Arg Gly Gly Leu Gly Gly Gln Gly Ala Gly Ala Ala Ala Ala
                85                  90                  95

Gly Gly Ala Gly Gln Gly Gly Tyr Gly Gly Leu Gly Ser Gln Gly Thr
                100                 105                 110

Ser Gly Arg Gly Gly Leu Gly Gly Gln Gly Ala Gly Ala Ala Ala
                115                 120                 125

Ala Gly Gly Ala Gly Gln Gly Gly Tyr Gly Gly Leu Gly Ser Gln Gly
            130                 135                 140

Thr Ser Gly Arg Gly Gly Leu Gly Gly Gln Gly Ala Gly Ala Ala Ala
145                 150                 155                 160

Ala Ala Gly Gly Ala Gly Gln Gly Gly Tyr Gly Gly Leu Gly Ser Gln
                165                 170                 175

Gly Thr Ser Gly Arg Gly Gly Leu Gly Gly Gln Gly Ala Gly Ala Ala
                180                 185                 190

Ala Ala Ala Gly Gly Ala Gly Gln Gly Gly Tyr Gly Gly Leu Gly Ser
            195                 200                 205

Gln Gly Thr Ser Gly Arg Gly Gly Leu Gly Gly Gln Gly Ala Gly Ala
    210                 215                 220

Ala Ala Ala Ala Gly Gly Ala Gly Gln Gly Gly Tyr Gly Gly Leu Gly
225                 230                 235                 240

Ser Gln Gly Thr Ser Gly Arg Gly Gly Leu Gly Gly Gln Gly Ala Gly
                245                 250                 255

Ala Ala Ala Ala Ala Gly Gly Ala Gly Gln Gly Gly Tyr Gly Gly Leu
            260                 265                 270

Gly Ser Gln Gly Thr Ser Gly Arg Gly Gly Leu Gly Gly Gln Gly Ala
    275                 280                 285

Gly Ala Ala Ala Ala Ala Gly Gly Ala Gly Gln Gly Gly Tyr Gly Gly
    290                 295                 300

Leu Gly Ser Gln Gly Thr Ser Gly Arg Gly Gly Leu Gly Gly Gln Gly
305                 310                 315                 320

Ala Gly Ala Ala Ala Ala Ala Gly Gly Ala Gly Gln Gly Gly Tyr Gly
                325                 330                 335

Gly Leu Gly Ser Gln Gly Thr Ser Gly Arg Gly Gly Leu Gly Gly Gln
            340                 345                 350

Gly Ala Gly Ala Ala Ala Ala Ala Gly Gly Ala Gly Gln Gly Gly Tyr
        355                 360                 365
```

```
Gly Gly Leu Gly Ser Gln Gly Thr Ser Gly Arg Gly Gly Leu Gly Gly
        370                 375                 380
Gln Gly Ala Gly Ala Ala Ala Ala Gly Gly Ala Gly Gln Gly Gly
385                 390                 395                 400
Tyr Gly Gly Leu Gly Ser Gln Gly Thr Ser Gly Arg Gly Gly Leu Gly
                405                 410                 415
Gly Gln Gly Ala Gly Ala Ala Ala Ala Gly Gly Ala Gly Gln Gly
            420                 425                 430
Gly Tyr Gly Gly Leu Gly Ser Gln Gly Thr Ser Gly Arg Gly Gly Leu
        435                 440                 445
Gly Gly Gln Gly Ala Gly Ala Ala Ala Ala Gly Gly Ala Gly Gln
450                 455                 460
Gly Gly Tyr Gly Gly Leu Gly Ser Gln Gly Thr Ser Gly Arg Gly Gly
465                 470                 475                 480
Leu Gly Gly Gln Gly Ala Gly Ala Ala Ala Ala Gly Gly Ala Gly
                485                 490                 495
Gln Gly Gly Tyr Gly Gly Leu Gly Ser Gln Gly Thr Ser Gly Arg Gly
                500                 505                 510
Gly Leu Gly Gly Gln Gly Ala Gly Ala Ala Ala Ala Gly Gly Ala
        515                 520                 525
Gly Gln Gly Gly Tyr Gly Gly Leu Gly Ser Gln Gly Thr Ser Met Ala
        530                 535                 540
Ala Thr Ser Ser Met Ser Val Glu Phe Tyr Asn Ser Asn Lys Ala Ala
545                 550                 555                 560
Gln Thr Asn Ser Ile Thr Pro Ile Ile Lys Ile Thr Asn Thr Ala Asp
                565                 570                 575
Ser Asp Leu Asn Leu Asn Asp Val Lys Val Arg Tyr Tyr Thr Ser
        580                 585                 590
Asp Gly Thr Gln Gly Gln Thr Phe Trp Gly Asp His Ala Gly Ala Leu
            595                 600                 605
Leu Gly Asn Ser Tyr Val Asp Asn Thr Gly Lys Val Thr Ala Asn Phe
        610                 615                 620
Val Lys Glu Thr Ala Ser Pro Thr Ser Thr Tyr Asp Thr Tyr Val Glu
625                 630                 635                 640
Phe Gly Phe Ala Ser Gly Ala Ala Thr Leu Lys Lys Gly Gln Phe Ile
                645                 650                 655
Thr Ile Gln Gly Arg Ile Thr Lys Ser Asp Trp Ser Asn Tyr Ala Gln
                660                 665                 670
Thr Asn Asp Tyr Ser Phe Asp Ala Ser Ser Thr Pro Val Val Asn
        675                 680                 685
Pro Lys Val Thr Gly Tyr Ile Gly Gly Ala Lys Val Leu Gly Thr Ala
        690                 695                 700
Pro Gly Pro Asp Val Pro Ser Ser Ile Ile Asn Pro Thr Ser Ala Thr
705                 710                 715                 720
Phe Asp Leu Glu His His His His His His
                725                 730

<210> SEQ ID NO 7
<211> LENGTH: 30
<212> TYPE: DNA
<213> ORGANISM: Artificial Sequence
<220> FEATURE:
<223> OTHER INFORMATION: Forward primer of CBD160
```

```
<400> SEQUENCE: 7
gactagtatg gcagcgacat catcaatgtc                                         30

<210> SEQ ID NO 8
<211> LENGTH: 38
<212> TYPE: DNA
<213> ORGANISM: Artificial Sequence
<220> FEATURE:
<223> OTHER INFORMATION: Reverse primer of CBD160

<400> SEQUENCE: 8
ctcgagatca aatgttgcag aagtaggatt aattattg                                38

<210> SEQ ID NO 9
<211> LENGTH: 6
<212> TYPE: PRT
<213> ORGANISM: Artificial Sequence
<220> FEATURE:
<223> OTHER INFORMATION: His6-containing sequence

<400> SEQUENCE: 9

His His His His His His
1               5

<210> SEQ ID NO 10
<211> LENGTH: 21
<212> TYPE: DNA
<213> ORGANISM: Artificial Sequence
<220> FEATURE:
<223> OTHER INFORMATION: DNA sequence encoding His N-terminal tag

<400> SEQUENCE: 10
caccatcatc atcatcatca t                                                  21

<210> SEQ ID NO 11
<211> LENGTH: 18
<212> TYPE: DNA
<213> ORGANISM: Artificial Sequence
<220> FEATURE:
<223> OTHER INFORMATION: DNA sequence encoding the C-terminal tag

<400> SEQUENCE: 11
caccaccacc accaccac                                                      18

<210> SEQ ID NO 12
<211> LENGTH: 16
<212> TYPE: PRT
<213> ORGANISM: Artificial Sequence
<220> FEATURE:
<223> OTHER INFORMATION: S-tag sequence

<400> SEQUENCE: 12

Met Lys Glu Thr Ala Ala Ala Lys Phe Glu Arg Gln His Met Asp Ser
1               5                   10                  15

<210> SEQ ID NO 13
<211> LENGTH: 1470
<212> TYPE: DNA
<213> ORGANISM: Nephila clavipes

<400> SEQUENCE: 13
agcggtcgtg gcggtctggg tggccagggt gcaggtgctg ctgcggcagc aggcggtgct        60
ggccaaggtg gctacggtgg cctgggttct caggtgtacta gcggtcgtgg cggtctgggt      120
ggccagggtg caggtgctgc tgcggcagca ggcggtgctg gccaaggtgg ctacggtggc       180
```

-continued

| | |
|---|---|
| ctgggttctc agggtactag cggtcgtggc ggtctgggtg gccagggtgc aggtgctgct | 240 |
| gcggcagcag gcggtgctgg ccaaggtggc tacggtggcc tgggttctca gggtactagc | 300 |
| ggtcgtggcg gtctgggtgg ccagggtgca ggtgctgctg cggcagcagg cggtgctggc | 360 |
| caaggtggct acggtggcct gggttctcag ggtactagcg gtcgtggcgg tctgggtggc | 420 |
| cagggtgcag gtgctgctgc ggcagcaggc ggtgctggcc aaggtggcta cggtggcctg | 480 |
| ggttctcagg gtactagcgg tcgtggcggt ctgggtggcc agggtgcagg tgctgctgcg | 540 |
| gcagcaggcg gtgctggcca aggtggctac ggtggcctgg gttctcaggg tactagcggt | 600 |
| cgtggcggtc tgggtggcca gggtgcaggt gctgctgcgg cagcaggcgg tgctggccaa | 660 |
| ggtggctacg gtggcctggg ttctcagggt actagcggtc gtggcggtct gggtggccag | 720 |
| ggtgcaggtg ctgctgcggc agcaggcggt gctggccaag gtggctacgg tggcctgggt | 780 |
| tctcaggagta ctagcggtcg tggcggtctg ggtggccagg gtgcaggtgc tgctgcggca | 840 |
| gcaggcggtg ctggccaagg tggctacggt ggcctgggtt ctcagggtac tagcggtcgt | 900 |
| ggcggtctgg gtgccagggg tgcaggtgct gctgcgcagca ggcggtgc tggccaaggt | 960 |
| ggctacggtg gcctgggttc tcagggtact agcggtcgtg gcggtctggg tggccagggt | 1020 |
| gcaggtgctg ctgcggcagc aggcggtgct ggccaaggtg gctacggtgg cctgggttct | 1080 |
| cagggtacta gcggtcgtgg cggtctgggt ggccagggtg caggtgctgc tgcggcagca | 1140 |
| ggcggtgctg gccaaggtgg ctacggtggc ctgggttctc agggtactag cggtcgtggc | 1200 |
| ggtctgggtg ccagggtgc aggtgctgct gcggcagcag gcggtgctgg ccaaggtggc | 1260 |
| tacggtggcc tgggttctca gggtactagc ggtcgtggcg gtctgggtgg ccagggtgca | 1320 |
| ggtgctgctg cggcagcagg cggtgctggc caaggtggct acggtggcct gggttctcag | 1380 |
| ggtactagcg gtcgtggcgg tctgggtggc cagggtgcag gtgctgctgc ggcagcaggc | 1440 |
| ggtgctggcc aaggtggcta cggtggcctg | 1470 |

<210> SEQ ID NO 14
<211> LENGTH: 490
<212> TYPE: PRT
<213> ORGANISM: Nephila clavipes

<400> SEQUENCE: 14

Ser Gly Arg Gly Gly Leu Gly Gly Gln Gly Ala Gly Ala Ala Ala
1               5                   10                  15

Ala Gly Gly Ala Gly Gln Gly Gly Tyr Gly Gly Leu Gly Ser Gln Gly
            20                  25                  30

Thr Ser Gly Arg Gly Gly Leu Gly Gly Gln Gly Ala Gly Ala Ala Ala
        35                  40                  45

Ala Ala Gly Gly Ala Gly Gln Gly Gly Tyr Gly Gly Leu Gly Ser Gln
    50                  55                  60

Gly Thr Ser Gly Arg Gly Gly Leu Gly Gly Gln Gly Ala Gly Ala Ala
65                  70                  75                  80

Ala Ala Ala Gly Gly Ala Gly Gln Gly Gly Tyr Gly Gly Leu Gly Ser
                85                  90                  95

Gln Gly Thr Ser Gly Arg Gly Gly Leu Gly Gly Gln Gly Ala Gly Ala
            100                 105                 110

Ala Ala Ala Ala Gly Gly Ala Gly Gln Gly Gly Tyr Gly Gly Leu Gly
        115                 120                 125

Ser Gln Gly Thr Ser Gly Arg Gly Gly Leu Gly Gly Gln Gly Ala Gly
    130                 135                 140

Ala Ala Ala Ala Ala Gly Gly Ala Gly Gln Gly Gly Tyr Gly Gly Leu
145                 150                 155                 160

Gly Ser Gln Gly Thr Ser Gly Arg Gly Gly Leu Gly Gly Gln Gly Ala
            165                 170                 175

Gly Ala Ala Ala Ala Gly Gly Ala Gly Gln Gly Gly Tyr Gly Gly
        180                 185                 190

Leu Gly Ser Gln Gly Thr Ser Gly Arg Gly Gly Leu Gly Gly Gln Gly
        195                 200                 205

Ala Gly Ala Ala Ala Ala Gly Gly Ala Gly Gln Gly Gly Tyr Gly
    210                 215                 220

Gly Leu Gly Ser Gln Gly Thr Ser Gly Arg Gly Gly Leu Gly Gly Gln
225                 230                 235                 240

Gly Ala Gly Ala Ala Ala Ala Gly Gly Ala Gly Gln Gly Gly Tyr
            245                 250                 255

Gly Gly Leu Gly Ser Gln Gly Thr Ser Gly Arg Gly Gly Leu Gly Gly
            260                 265                 270

Gln Gly Ala Gly Ala Ala Ala Ala Gly Gly Ala Gly Gln Gly Gly
        275                 280                 285

Tyr Gly Gly Leu Gly Ser Gln Gly Thr Ser Gly Arg Gly Gly Leu Gly
        290                 295                 300

Gly Gln Gly Ala Gly Ala Ala Ala Ala Gly Gly Ala Gly Gln Gly
305                 310                 315                 320

Gly Tyr Gly Gly Leu Gly Ser Gln Gly Thr Ser Gly Arg Gly Gly Leu
            325                 330                 335

Gly Gly Gln Gly Ala Gly Ala Ala Ala Ala Gly Gly Ala Gly Gln
        340                 345                 350

Gly Gly Tyr Gly Gly Leu Gly Ser Gln Gly Thr Ser Gly Arg Gly Gly
        355                 360                 365

Leu Gly Gly Gln Gly Ala Gly Ala Ala Ala Ala Gly Gly Ala Gly
    370                 375                 380

Gln Gly Gly Tyr Gly Gly Leu Gly Ser Gln Gly Thr Ser Gly Arg Gly
385                 390                 395                 400

Gly Leu Gly Gly Gln Gly Ala Gly Ala Ala Ala Ala Gly Gly Ala
            405                 410                 415

Gly Gln Gly Gly Tyr Gly Gly Leu Gly Ser Gln Gly Thr Ser Gly Arg
            420                 425                 430

Gly Gly Leu Gly Gly Gln Gly Ala Gly Ala Ala Ala Ala Gly Gly
        435                 440                 445

Ala Gly Gln Gly Gly Tyr Gly Gly Leu Gly Ser Gln Gly Thr Ser Gly
    450                 455                 460

Arg Gly Gly Leu Gly Gly Gln Gly Ala Gly Ala Ala Ala Ala Gly
465                 470                 475                 480

Gly Ala Gly Gln Gly Gly Tyr Gly Gly Leu
            485                 490

<210> SEQ ID NO 15
<211> LENGTH: 2028
<212> TYPE: DNA
<213> ORGANISM: Artificial Sequence
<220> FEATURE:
<223> OTHER INFORMATION: DNA Encoding the spider-silk-CBD chimeric
      polypeptide

```
<400> SEQUENCE: 15
agcggtcgtg gcggtctggg tggccagggt gcaggtgctg ctgcggcagc aggcggtgct      60
ggccaaggtg gctacggtgg cctgggttct cagggtacta gcggtcgtgg cggtctgggt     120
ggccagggtg caggtgctgc tgcggcagca ggcggtgctg gccaaggtgg ctacggtggc     180
ctgggttctc agggtactag cggtcgtggc ggtctgggtg ccagggtgca ggtgctgct      240
gcggcagcag gcggtgctgg ccaaggtggc tacggtggcc tgggttctca gggtactagc     300
ggtcgtggcg gtctgggtgg ccagggtgca ggtgctgctg cggcagcagg cggtgctggc     360
caaggtggct acggtggcct gggttctcag ggtactagcg gtcgtggcgg tctgggtggc     420
cagggtgcag gtgctgctgc ggcagcaggc ggtgctggcc aaggtggcta cggtggcctg     480
ggttctcagg gtactagcgg tcgtggcggt ctgggtggcc agggtgcagg tgctgctgcg     540
gcagcaggcg gtgctggcca aggtggctac ggtggcctgg gttctcaggg tactagcggt     600
cgtggcggtc tgggtggcca gggtgcaggt gctgctgcgg cagcaggcgg tgctggccaa     660
ggtggctacg gtggcctggg ttctcagggt actagcggtc gtggcggtct gggtggccag     720
ggtgcaggtg ctgctgcggc agcaggcggt gctggccaag gtggctacgg tggcctgggt     780
tctcagggta ctagcggtcg tggcggtctg ggtggccagg gtgcaggtgc tgctgcggca     840
gcaggcggtg ctggccaagg tggctacggt ggcctgggtt ctcagggtac tagcggtcgt     900
ggcggtctgg gtgccagggt gcaggtgct gctgcgcag caggcggtgc tggccaaggt     960
ggctacggtg gcctgggttc tcagggtact agcggtcgtg gcggtctggg tggccagggt    1020
gcaggtgctg ctgcggcagc aggcggtgct ggccaaggtg gctacggtgg cctgggttct    1080
cagggtacta gcggtcgtgg cggtctgggt ggccagggtc aggtgctgc tgcggcagca    1140
ggcggtgctg gccaaggtgg ctacggtggc ctgggttctc agggtactag cggtcgtggc    1200
ggtctgggtg ccagggtgc aggtgctgct gcggcagcag gcggtgctgg ccaaggtggc    1260
tacggtggcc tgggttctca gggtactagc ggtcgtggcg gtctgggtgg ccagggtgca    1320
ggtgctgctg cggcagcagg cggtgctggc caaggtggct acggtggcct gggttctcag    1380
ggtactagcg gtcgtggcgg tctgggtggc cagggtgcag gtgctgctgc ggcagcaggc    1440
ggtgctggcc aaggtggcta cggtggcctg gttctcagg gtactagtat ggcagcgaca    1500
tcatcaatgt cagttgaatt ttacaactct aacaaagcag cacaaacaaa ctcaattaca    1560
ccaataatca aaattactaa cacagctgac agtgatttaa atttaaatga cgtaaaagtt    1620
agatattatt acacaagtga tggtacacaa ggacaaactt tctggggtga tcatgctggt    1680
gcattattag aaatagcta tgttgataac actggcaaag tgacagcaaa cttcgttaaa    1740
gaaacagcaa gcccaacatc aacctatgat acatatgttg aatttggatt tgcaagcgga    1800
gcagctactc ttaaaaaagg acaatttata actattcaag gaagaataac aaaatcagac    1860
tggtcaaact acgctcagac aaatgactat tcatttgatg caagtagttc aacaccagtt    1920
gtaaatccaa aagttacagg atatataggt ggagctaaag tacttggtac agcaccaggt    1980
ccagatgtac catcttcaat aattaatcct acttctgcaa catttgat                 2028
```

<210> SEQ ID NO 16
<211> LENGTH: 676
<212> TYPE: PRT
<213> ORGANISM: Artificial Sequence
<220> FEATURE:
<223> OTHER INFORMATION: spider-silk-CBD chimeric polypeptide

<400> SEQUENCE: 16

```
Ser Gly Arg Gly Gly Leu Gly Gly Gln Gly Ala Gly Ala Ala Ala
1               5                   10                  15

Ala Gly Gly Ala Gly Gln Gly Gly Tyr Gly Gly Leu Gly Ser Gln Gly
            20                  25                  30

Thr Ser Gly Arg Gly Gly Leu Gly Gly Gln Gly Ala Gly Ala Ala Ala
        35                  40                  45

Ala Ala Gly Gly Ala Gly Gln Gly Gly Tyr Gly Gly Leu Gly Ser Gln
    50                  55                  60

Gly Thr Ser Gly Arg Gly Gly Leu Gly Gly Gln Gly Ala Gly Ala Ala
65                  70                  75                  80

Ala Ala Ala Gly Gly Ala Gly Gln Gly Gly Tyr Gly Gly Leu Gly Ser
                85                  90                  95

Gln Gly Thr Ser Gly Arg Gly Gly Leu Gly Gly Gln Gly Ala Gly Ala
            100                 105                 110

Ala Ala Ala Ala Gly Gly Ala Gly Gln Gly Gly Tyr Gly Gly Leu Gly
        115                 120                 125

Ser Gln Gly Thr Ser Gly Arg Gly Gly Leu Gly Gly Gln Gly Ala Gly
    130                 135                 140

Ala Ala Ala Ala Ala Gly Gly Ala Gly Gln Gly Gly Tyr Gly Gly Leu
145                 150                 155                 160

Gly Ser Gln Gly Thr Ser Gly Arg Gly Gly Leu Gly Gly Gln Gly Ala
                165                 170                 175

Gly Ala Ala Ala Ala Gly Gly Ala Gly Gln Gly Gly Tyr Gly Gly
            180                 185                 190

Leu Gly Ser Gln Gly Thr Ser Gly Arg Gly Gly Leu Gly Gly Gln Gly
        195                 200                 205

Ala Gly Ala Ala Ala Ala Gly Gly Ala Gly Gln Gly Gly Tyr Gly
    210                 215                 220

Gly Leu Gly Ser Gln Gly Thr Ser Gly Arg Gly Gly Leu Gly Gly Gln
225                 230                 235                 240

Gly Ala Gly Ala Ala Ala Ala Gly Gly Ala Gly Gln Gly Gly Tyr
                245                 250                 255

Gly Gly Leu Gly Ser Gln Gly Thr Ser Gly Arg Gly Gly Leu Gly Gly
            260                 265                 270

Gln Gly Ala Gly Ala Ala Ala Ala Gly Gly Ala Gly Gln Gly Gly
        275                 280                 285

Tyr Gly Gly Leu Gly Ser Gln Gly Thr Ser Gly Arg Gly Gly Leu Gly
    290                 295                 300

Gly Gln Gly Ala Gly Ala Ala Ala Ala Gly Gly Ala Gly Gln Gly
305                 310                 315                 320

Gly Tyr Gly Gly Leu Gly Ser Gln Gly Thr Ser Gly Arg Gly Gly Leu
                325                 330                 335

Gly Gly Gln Gly Ala Gly Ala Ala Ala Ala Gly Gly Ala Gly Gln
            340                 345                 350

Gly Gly Tyr Gly Gly Leu Gly Ser Gln Gly Thr Ser Gly Arg Gly Gly
        355                 360                 365

Leu Gly Gly Gln Gly Ala Gly Ala Ala Ala Ala Gly Gly Ala Gly
    370                 375                 380

Gln Gly Gly Tyr Gly Gly Leu Gly Ser Gln Gly Thr Ser Gly Arg Gly
385                 390                 395                 400

Gly Leu Gly Gly Gln Gly Ala Gly Ala Ala Ala Ala Gly Gly Ala
                405                 410                 415
```

-continued

```
Gly Gln Gly Gly Tyr Gly Gly Leu Gly Ser Gln Gly Thr Ser Gly Arg
            420                 425                 430
Gly Gly Leu Gly Gly Gln Gly Ala Gly Ala Ala Ala Ala Ala Gly Gly
            435                 440                 445
Ala Gly Gln Gly Gly Tyr Gly Gly Leu Gly Ser Gln Gly Thr Ser Gly
450                 455                 460
Arg Gly Gly Leu Gly Gly Gln Gly Ala Gly Ala Ala Ala Ala Ala Gly
465                 470                 475                 480
Gly Ala Gly Gln Gly Gly Tyr Gly Gly Leu Gly Ser Gln Gly Thr Ser
                485                 490                 495
Met Ala Ala Thr Ser Ser Met Ser Val Glu Phe Tyr Asn Ser Asn Lys
            500                 505                 510
Ala Ala Gln Thr Asn Ser Ile Thr Pro Ile Ile Lys Ile Thr Asn Thr
            515                 520                 525
Ala Asp Ser Asp Leu Asn Leu Asn Asp Val Lys Val Arg Tyr Tyr Tyr
            530                 535                 540
Thr Ser Asp Gly Thr Gln Gly Gln Thr Phe Trp Gly Asp His Ala Gly
545                 550                 555                 560
Ala Leu Leu Gly Asn Ser Tyr Val Asp Asn Thr Gly Lys Val Thr Ala
                565                 570                 575
Asn Phe Val Lys Glu Thr Ala Ser Pro Thr Ser Thr Tyr Asp Thr Tyr
                580                 585                 590
Val Glu Phe Gly Phe Ala Ser Gly Ala Ala Thr Leu Lys Lys Gly Gln
            595                 600                 605
Phe Ile Thr Ile Gln Gly Arg Ile Thr Lys Ser Asp Trp Ser Asn Tyr
            610                 615                 620
Ala Gln Thr Asn Asp Tyr Ser Phe Asp Ala Ser Ser Ser Thr Pro Val
625                 630                 635                 640
Val Asn Pro Lys Val Thr Gly Tyr Ile Gly Gly Ala Lys Val Leu Gly
                645                 650                 655
Thr Ala Pro Gly Pro Asp Val Pro Ser Ser Ile Ile Asn Pro Thr Ser
            660                 665                 670
Ala Thr Phe Asp
            675
```

HIGH MOLECULAR ORDERED FIBRILAR STRUCTURES, METHOD FOR THEIR PREPARATION AND USES THEREOF

CROSS-REFERENCE TO RELATED APPLICATIONS AND CLAIM TO PRIORITY

This application is a §371 National Stage Application of PCT/IL2012/000058 (filed on Feb. 2, 2012), which application claims priority to U.S. patent application Ser. No. 61/439,120 (filed on Feb. 3, 2011), each of which applications is herein incorporated by reference in its entirety and to which priority is claimed.

FIELD OF THE INVENTION

The present invention relates to methods for generation of high molecular ordered fibrilar structures. More particularly, the method of the invention utilizes CBD's (cellulose binding domain) ability to form dimers for directing ordered assembly of fibrous proteins such as silk proteins into super-molecular fibrilar structures.

BACKGROUND OF THE INVENTION

All publications mentioned throughout this application are fully incorporated herein by reference, including all references cited therein.

Biomolecules in general and proteins in particular are capable of self-assembling into a wide variety of structures that can be readily manipulated and functionalized. Today there is an exceeding demand in the field of nano-biotechnology and material science for a reliable, highly stable building block that can self assemble to form higher hierarchy ordered compounds.

Biopolymer research has focused in recent years on fibrous proteins due to their unique mechanical properties. For example, one can mention the mammalian collagen and elastin and the arthropod proteins, silk worm silk (*Bombyx morii*), spider dragline silk and resilin. These proteins are distinguished by their repetitive amino acid sequences that confer their mechanical properties such as strength and flexibility. For instance spider silk is extremely strong while resilin and elastin are extremely stretchy/elastic and resilient and have a rubber like nature. The unique repetitive sequence of each protein confers its three-dimensional architecture and mechanical properties. Much can be learned from the organizational principles employed in native biopolymers. Substantial progress has been made in the elucidation of the three-dimensional architectures of spider silks and collagens. Still, an important challenge is the translation of these concepts into synthetic or bio-inspired materials, which would lead to new kinds of high performance fibers. The translation process requires a level of control of macromolecular architecture far higher than that afforded by conventional polymerization processes. These biomaterials could replace, in part, synthetic plastics, fibers and elastomers, thus offering the advantage of renewability, sustainability and biodegradability.

Cellulose is degraded in nature by the concerted action of a number of bacterial and fungal organisms. The initial event in the degradation process is the binding of the cellulolytic enzyme(s) or the entire microorganism to the cellulose substrate. A separate domain, named CBD, mediates this binding. The CBD enables adhesion of the water soluble enzyme onto an insoluble substrate surface (cellulose). The close association between the enzyme and cellulose provided by the CBD enhances the catalytic rate and stability of the enzyme. A wide variety of CBDs are known, having different binding constants as well as sensitivity to heat and pH. The binding domains are classified into 61 different families (see http://www.cazy.org), based on amino acid sequences, binding specificity, and structure. The binding of *Clostridium cellulovorans* CBD (CBDclos, family III) is unique in the manner in which it maintains its specific cellulose binding properties under conditions which most proteins are denatured and nonfunctional. The CBDcex from *Cellulomonas fimi* (family II) binds to many forms of insoluble cellulose, including amorphous, semi-crystalline, and crystalline and was applied in a variety of fusion proteins.

It is well known that some kinds of CBDs form dimers or higher molecular weight compounds in solution or upon binding to cellulose. Different proteins fused to CBDclos were expressed in *E. coli* and were shown to form dimers in solution [Xu Y. et al., J. Biotechnol. 135: 319-25 (2008)]. Chromatography, ultracentrifugation and 15N NMR relaxation experiments demonstrate that CBDcex is a dimer in solution [Xu G. Y. et al., Biochemistry 34:6993-7009 (1995)].

Silk proteins are produced by a variety of insects and arachnids, the latter of which form the strongest silk polymers on earth. The spider spins as many as seven different kinds of silks, each one being optimized to its specific biological function in nature. Dragline silk, used as the safety line and as the frame thread of the spider's web, is an impressive material with a combination of tensile strength and elasticity. These properties endow it with unique toughness which displays the highest energy to break among common natural or artificial materials. The dragline fiber is predominantly proteineacous, comprised of greater than 80% glycine, alanine and other short side chain amino acids with crystalline regions of antiparallel β-pleated sheets. The dragline fiber's extraordinary properties are derived from its composition as a semicrystalline polymer, comprising crystalline regions embedded in a less organized "amorphous" matrix. The antiparallel β-pleated sheets of polyalanine stretches give strength to the thread, while the predominant secondary structure of the amorphous matrix is the glycine-rich helix which provides elasticity. Most dragline silks consist of at least two different proteins with molecular masses of up to several hundred kDa.

Numerous gene sequences coding for spider type silks are known [Gatesy et al., Science 291:2603-2605 (2001)]. An examination of the cDNAs, genes and amino acid sequences shows that all silks are chains of iterated peptide motifs. The consensus sequences for the repeating peptides are repeated multiple times throughout the core of each protein, flanked by non repetitive, highly conserved, short terminal sequences. On the basis of sequence similarities, dragline silk proteins have been grouped into spidroin1-like (MaSp1) and spidroin2-like (MaSp2) proteins.

As opposed to silkworm silk, isolation of silk from spiders is not industrially feasible. Spiders produce silk in small quantities, and their territorial behavior prevents large amounts thereof from being harvested in adjacent quarters. Therefore, production of silk protein through recombinant DNA techniques is preferred. For such purposes, widespread use is made of synthetic genes based on a monomer consensus of the native spidroin sequences. These synthetic genes have been successfully expressed in the methyltropic yeast host, *Pichia pastoris*, in *E. coli* and in the tobacco and potato plants [Fahnestock et al., Appl. Microbiol. Biotechnol. 47:33-39 (1997); Fahnestock et al., Appl. Microbiol. Biotechnol. 47:23-32 (1997); Sceller et al., Nature biotechnology 19:573-577 (2001)]. Through such means, laboratory scale amounts of silk-like protein powders are readily available. The final hurdle on the way to the production of manmade silks lies in the development of an appropriate spinning technology capable of converting these powders into high performance fibers. A significant limitation toward successfully producing functional silk has been the tendency of these proteins to aggregate in-vitro, bypassing the protein folding process. The assembly of the proteins in a liquid crystalline form into a solid silk string is extremely complex, and duplication of the operational function of spider spinning glands is a major challenge. The present inventors have previously shown generation of composites comprising fusion of fibrous proteins to CBD attached to cellulose [US 2010/0317588].

The present invention now discloses a method utilizing CBD's ability to form dimers or higher molecular weight compounds in order to direct molecular order and assembly of CBD fusion proteins. The invention specifically demonstrates CBD's ability to create higher hierarchy ordering by its fusion to dragline spider silk proteins.

Thus, one object of the invention is to provide a method for generating high molecular ordered fibrilar structures by directing ordered assembly of fibrous proteins.

Another object of the invention is to provide isolated high molecular ordered fibrilar structures.

Still further the invention provides the use of the fibrilar structures in medicine, in reconstruction of tissues, as scaffolds for growth of cells, as support for bone, ligaments and tendon, and/or as parts of implantable medical device. The invention further provides the use of these fibrilar structures in the military and avian industry where high strength and low weight are important, e.g. in unmanned aerial vehicle, in personal armor and the like.

These and other objects of the invention will become apparent as the description proceeds.

SUMMARY OF THE INVENTION

According to a first aspect, the invention relates to a method for generating high molecular ordered fibrilar structures by directing ordered assembly of fibrous proteins. The method of the invention comprises the following steps, first, in step (a) providing at least one fibrous protein monomer. In step (b) at least one heterologous polysaccharide binding domain is provided. In the next step (c) both elements, the at least one fibrous protein monomer provided in (a) and the heterologous polysaccharide binding domain provided in (b) are attached together thereby obtaining a polypeptide comprising an amino acid sequence of a fibrous protein monomer attached to a heterologous polysaccharide binding domain. The next step (d) involves providing a solution of the isolated polypeptide obtained in (c), optionally by admixing the polypeptide in a solution under conditions which allow folding of said fibrous protein to generate the fibrilar structures. Finally in step (e), the method requires recovering the fibrilar structures from the solution, thereby obtaining isolated high molecular ordered fibrilar structures.

A second aspect of the invention relates to an isolated high molecular ordered fibrilar structure consisting of at least one isolated polypeptide comprising an amino acid sequence of fibrous protein monomer attached to a heterologous polysaccharide binding domain.

In a third aspect, the present invention relates to a fiber consisting of at least one isolated polypeptide comprising an amino acid sequence of fibrous protein monomer attached to a heterologous polysaccharide binding domain.

The invention further provides a scaffold comprising the isolated fibrilar structure of the invention.

Another aspect of the invention relates to a method of preparing a scaffold comprising at least one high molecular ordered fibrilar structure consisting of at least one isolated polypeptide comprising an amino acid sequence of fibrous protein monomer attached to a heterologous polysaccharide binding domain. The method comprises the steps of:

(a) providing a solution of at least one high molecular ordered fibrilar structures. It should be appreciated that these fibrilar structures are prepared by the method of the invention. The next step (b) involves purring the fibrilar structures solution into a mold; and (c) maintaining the mold under conditions which allow the formation of said scaffold.

Another aspect of the invention relates to a pharmaceutical composition comprising as an active ingredient the high molecular ordered fibrilar structure of the invention.

In yet further embodiments, the composition of the invention may be a cosmetic composition.

An additional aspect of the invention relates to an article comprising at least one isolated high molecular ordered fibrilar structure of the invention.

These and other aspects of the invention will become apparent by the hand of the following figures.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE FIGURES

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

FIG. 1. DNA and protein sequence of 6H-15mer

This is an illustration of the DNA and protein sequence of the 6H-15mer used to create the silk-CBD fusion protein of the invention: the His tag is underlined; the dashed underline marks the s-tag; the double underline marks the representative monomeric silk unit; and Italic represents amino acids added from the cloning process. The nucleotide sequence is denoted by SEQ ID NO. 1 and the amino acid sequence is denoted by SEQ ID NO. 2.

FIG. 2. DNA and protein sequence of CBDclos

This is an illustration of the DNA and protein-sequence of the CBDclos used to create the silk-CBD fusion protein of the invention. The nucleotide sequence is denoted by SEQ ID NO. 3 and the amino acid sequence are denoted by SEQ ID NO. 4.

FIG. 3. Construction of silk-CBD fusion gene

Schematic description of the 15mer construct provided in a pET30a vector. The scheme shows location of the restriction enzymes used for the cloning procedure.

Abbreviations: 6H (the six histidine tag), S. (Silk).

Figure 4:
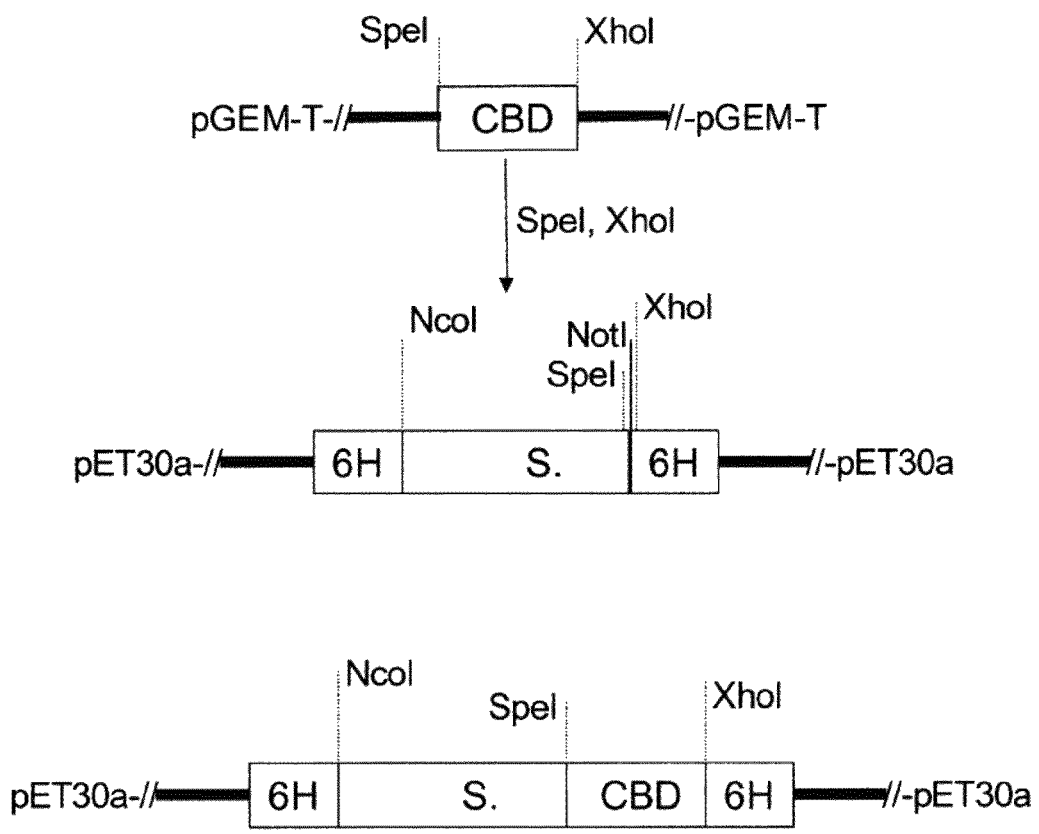

FIG. 4. Cloning of SpeI-CBDclos-XhoI into pET30a-15mer

Schematic description of 15mer-CBD cloning procedure. The scheme shows location of the restriction enzymes used for the cloning procedure.

Abbreviations: 6H (the six histidine tag), S. (Silk), CBD (cellulose binding domain).

Figure 5:
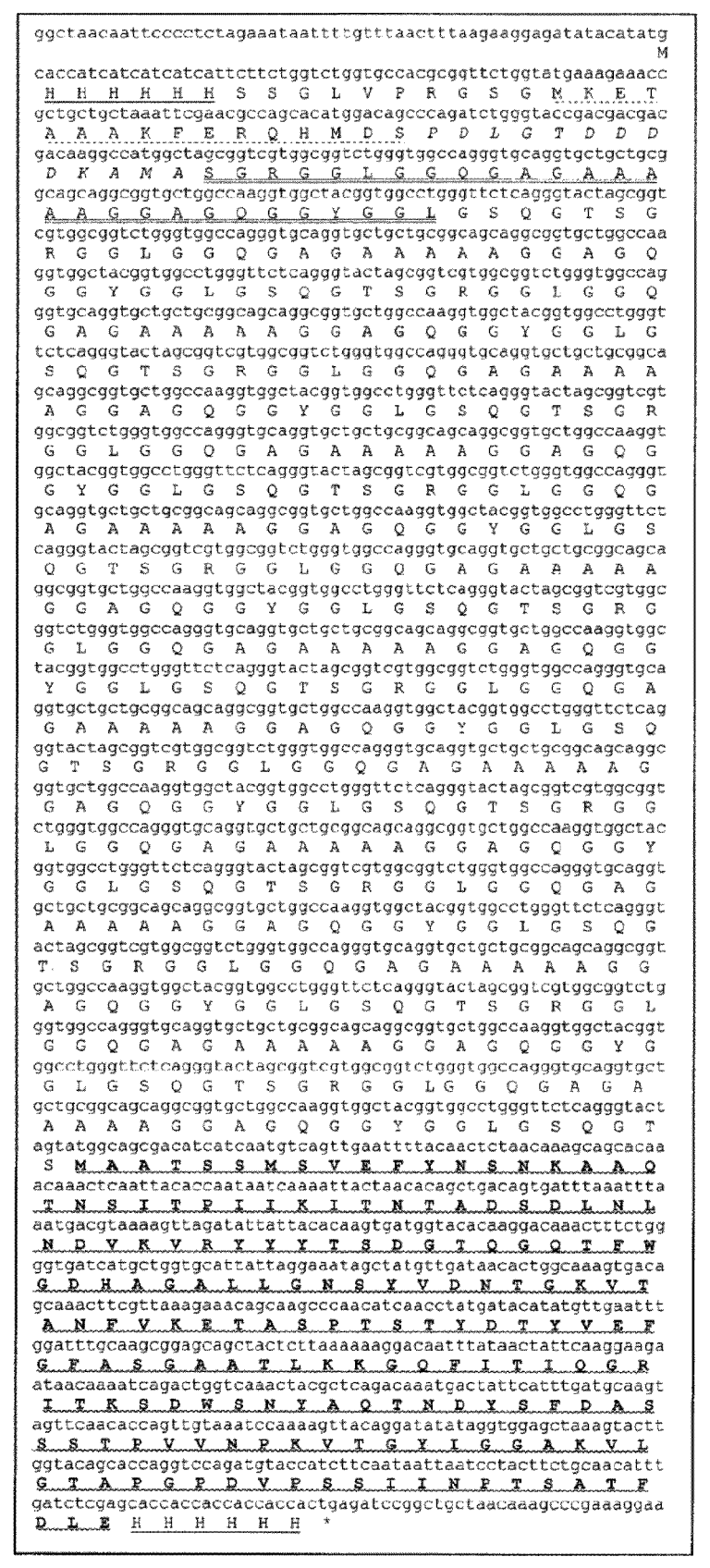

FIG. 5. DNA and protein sequence of 6H-15mer-CBD

This is an illustration of the DNA- and protein-sequence of the 6H-15mer-CBD fusion protein: the His tag is underlined; the dashed underline marks the s-tag; the double underline marks the representative monomeric silk unit; and Bold wave underline represents the CBD sequence. The nucleotide sequence is denoted by SEQ ID NO. 5 and the amino acid sequence are denoted by SEQ ID NO. 6.

Figure 6:
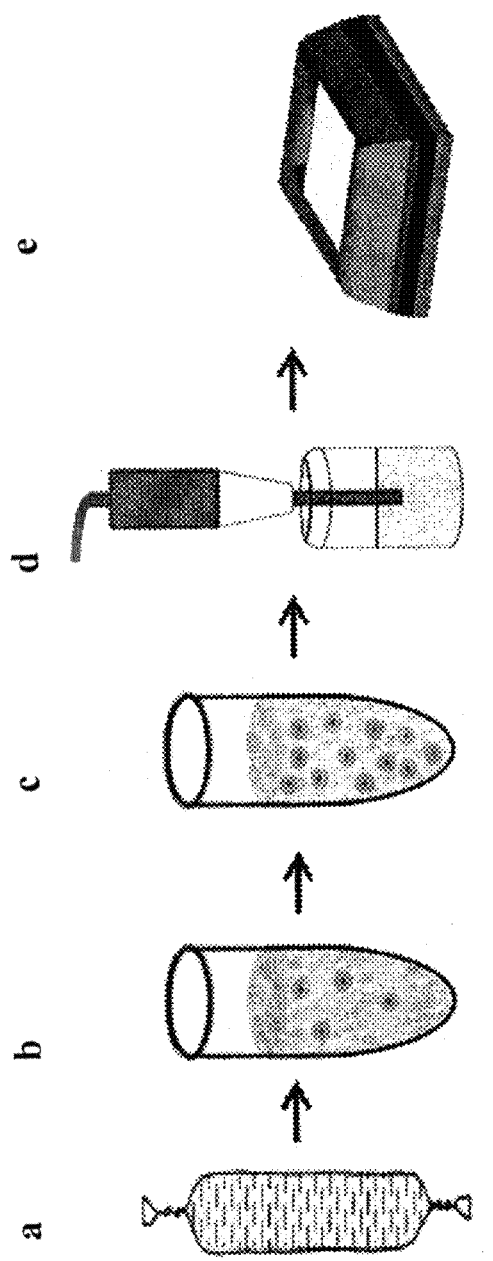

FIG. 6. Production of spider silk composite sponges

Purified 15mer/15mer-CBD protein was dialyzed against water (A+B), the protein aqueous solution was concentrated (C), exposed to sonication (D), and purred into a Teflon mold (E).

Figure 7:
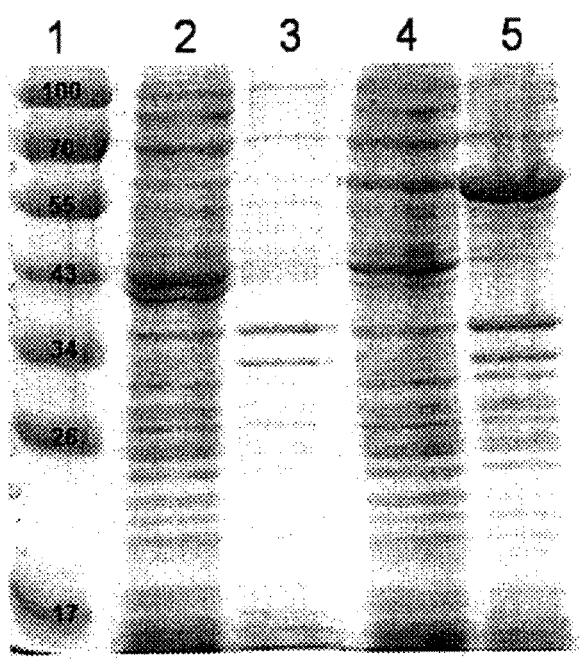

FIG. 7. Expression of dragline silk and dragline silk-CB-Dclos proteins in E. coli SDS-PAGE analyses of 6H-Silk and 6H-Silk-CBD expressed in E. Coli: E. coli lysates were resolved by SDS/PAGE and stained with Coomassie blue: Lane 1 is the molecular weight marker (numbers are in kDa); Lanes 2 & 4 are soluble E. coli protein fractions of Silk and Silk-CBD expressing bacteria, respectively; and Lanes 3 & 5 are insoluble E. coli protein fractions of Silk and Silk-CBD expressing bacteria, respectively.

Figure 8A:
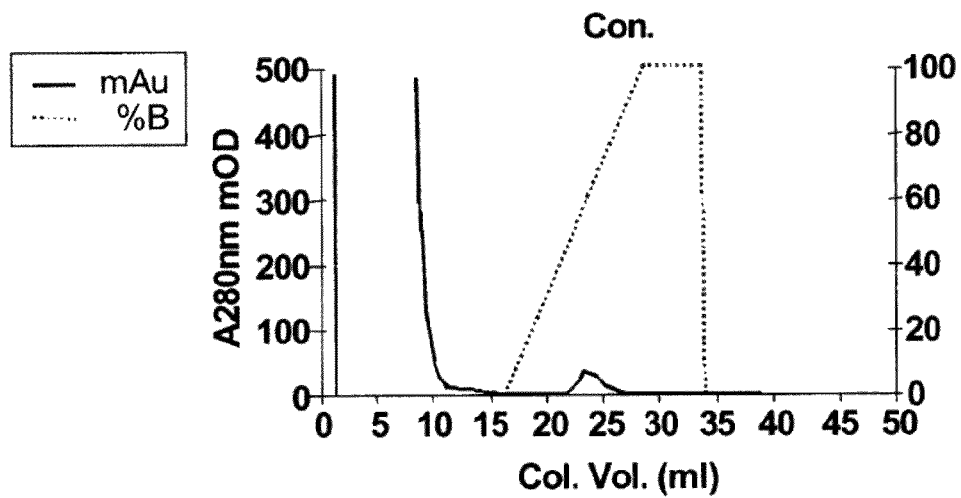
Figure 8B:
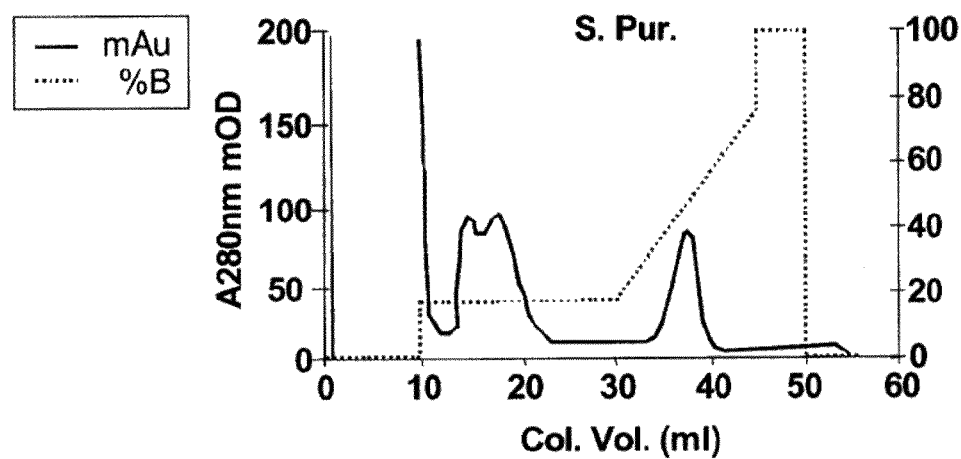
Figure 8C:
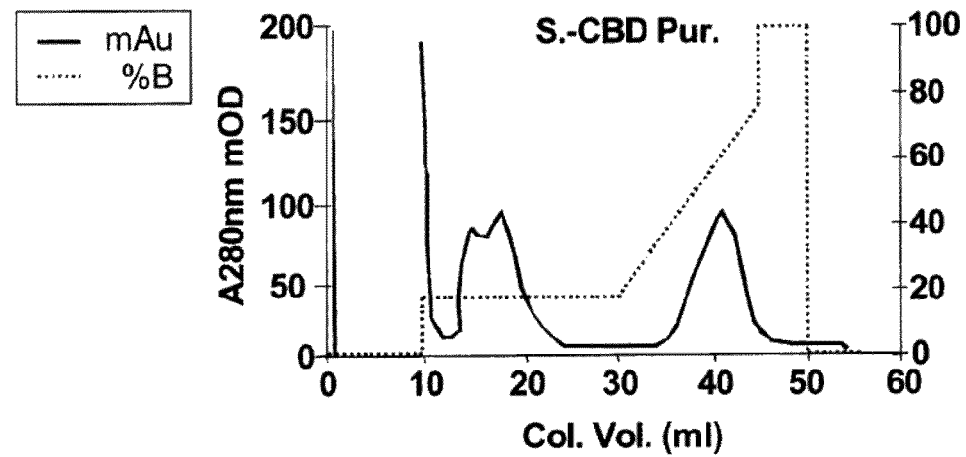

FIG. 8A-8C. Chromatograms illustrating FPLC purification of 6H-dragline silk and 611-dragline silk-CBD Silk proteins produced from E. coli were purified on a Ni-NTA column:

FIG. 8A. Ni-NTA purification chromatogram of control E. coli proteins transformed with a non containing insert vector.

FIG. 8B. Ni-NTA purification chromatogram of E. coli transformed with vector encoding Silk proteins.

FIG. 8C. Ni-NTA purification chromatogram of E. coli transformed with vector encoding Silk-CBD proteins.

Abbreviations: Con. (control), Col. Vol. (column volume), S. Pur. (Silk purification), S.-CBD Pur. (Silk-cellulose-binding-domain purification).

Figure 9A:
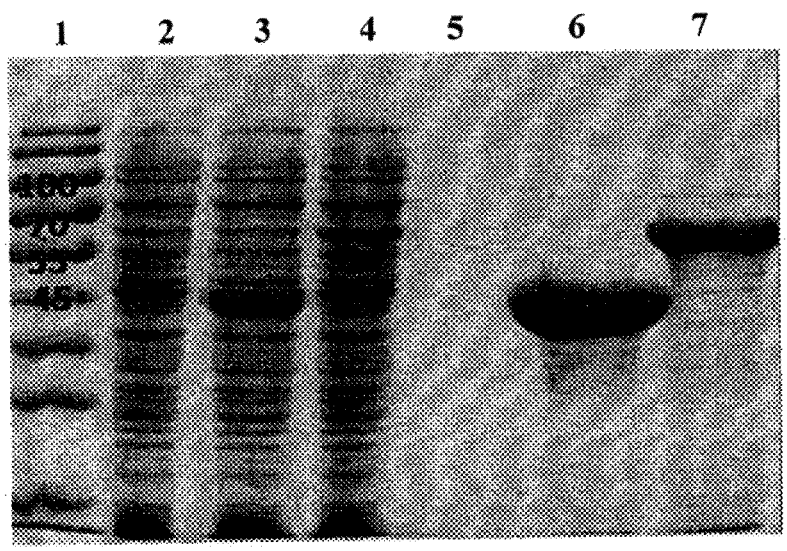

FIG. 9A-8B. SDS-PAGE analysis of soluble E. coli proteins

SDS-PAGE analyses of E. Coli expressing 6H-Silk and 6H-Silk-CBD proteins. Lane 1 is protein molecular weight marker (kDa); Lanes 2-4 are total protein lysate from control-, Silk-, and Silk-CBD-expressing E. coli, respectfully; Lanes 5-7 are the Ni-NTA purified proteins from the same control-, Silk-, Silk-CBD-expressing E. coli lysates, respectively.

FIG. 9A. Coomassie blue staining of the SDS-PAGE gel.

Figure 9B:
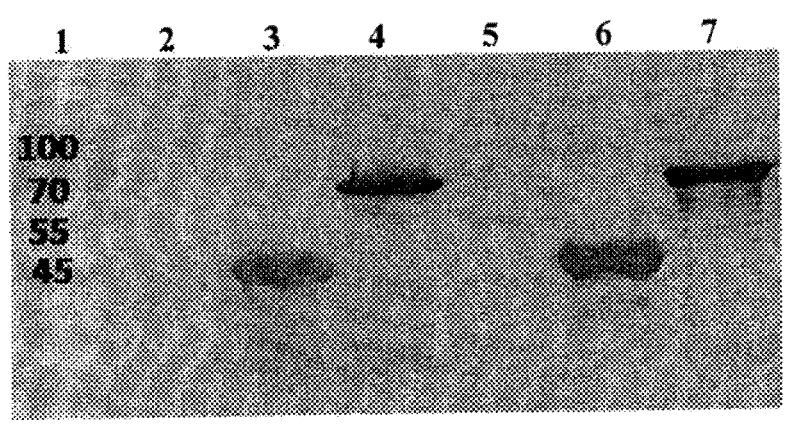

FIG. 9B. Western blot analysis of the same samples of FIG. 9A, with anti-HIS antibodies.

FIG. 10A-10D. Gel filtration FPLC of dragline-silk and dragline silk-CBD proteins before and after sonication FIG. 10A. A graph representing gel filtration of Silk protein samples before (continues line) and after (dashed line) sonication.

FIG. 10B. A graph representing gel filtration of Silk-CBD protein samples before (continues line) and after (dashed line) sonication.

FIG. 10C. shows an SDS-PAGE analysis of gel filtration fractions of sonicated Silk samples.

FIG. 10D. shows an SDS-PAGE analysis of gel filtration fractions of sonicated Silk-CBD samples.

Abbreviations: Vol. (ml) (volume in milliliters), S (Silk), S.-CBD (Silk-cellulose-binding-domain), S.-Son (Silk-sonicated), S.-CBD-Son (Silk-cellulose-binding-domain sonicated), O.D. (optical density).

FIG. 11A-11C. Solution X-ray scattering of dragline silk and dragline silk-CBD proteins Radially integrated measured scattering intensity from silk/silk-CBD non-concentrated and concentrated (C) samples at room temperature before (FIG. 11A) and after sonication (FIG. 11B and FIG. 11C).

Abbreviations: Int. (Intensity), Wa. (water), S (Silk), S.C. (Silk concentrated), S.-CBD (Silk-cellulose-binding-domain), CBD (cellulose-binding-domain), CBD C (cellulose-binding-domain concentrated), S.-CBD C (Silk-cellulose-binding-domain concentrated), son. Sam (sonicated sample).

FIG. 12A-12F. Schematic illustration of silk-CBD in non-concentrated and concentrated samples based on Solution X-ray scattering FIG. 12A, FIG. 12B, FIG. 12D and FIG. 12E. Schematic illustration of the silk-CBD measured ordered hierarchy in non-concentrated (FIG. 12A and FIG. 12D) and concentrated (FIG. 12B and FIG. 12E) samples before (FIG. 12A-12B) and after sonication (FIG. 12D-12E).

FIG. 12C and FIG. 12F. Model structure of silk-CBD self assembled subunits before (FIG. 12C) and after (FIG. 12F) sonication.

Abbreviations: Con. Sam. (concentrated sample).

FIG. 13A-13F. TEM pictures of silk-CBD fibers

Cryo-TEM images of silk (FIGS. 13A and 13B) and silk-CBD (FIGS. 13C to 13F) sonicated solutions.

The scale bar of FIGS. 13A-13C and FIGS. 13E to 13F is 60 nm, whereas the scale bar of picture d is 100 nm.

Abbreviations: S (Silk), S.-CBD (Silk-cellulose-binding-domain).

DETAILED DESCRIPTION OF THE INVENTION

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Proteins are capable of self-assembling into a wide variety of structures that can be readily manipulated and functionalized for use in various ways. Today there is an exceeding demand in the field of nano-biotechnology and material science for a reliable, highly stable building block that can self assemble to form higher hierarchy ordered compounds. However, fibrilar structures, especially silk fibrilar structures, are very difficult to produce recombinantly in soluble form. Most known techniques to produce artificial silk fibers are complicated and have many disadvantages, and result with a very low yield.

In a search to identify novel biomaterials with superior mechanical properties for use in medical, industrial and other applications, the present inventors have generated high molecular fibrilar structures utilizing various polysaccharide binding domains. More specifically, the present invention is the first to utilize the ability of CBD (cellulose binding domain) to form dimers or higher molecular weight compounds for the assembly of fusion proteins and the formation of higher molecular fibrilar structures.

Therefore, in a first aspect, the invention relates to a method for generating high molecular ordered fibrilar structures by directing ordered assembly of fibrous proteins. The method of the invention comprises the following steps, first, in step (a)

providing at least one fibrous protein monomer. In step (b) at least one heterologous polysaccharide binding domain is provided. In the next step (c) both elements, the at least one fibrous protein monomer provided in (a) and the heterologous polysaccharide binding domain provided in (b) are attached together thereby obtaining a polypeptide comprising an amino acid sequence of a fibrous protein monomer attached to a heterologous polysaccharide binding domain. The next step (d) involves providing a solution of the isolated polypeptide obtained in (c), optionally by admixing the polypeptide in a solution under conditions which allow folding of said fibrous protein to generate the fibrilar structures. Finally in step (e), the method requires recovering the fibrilar structures from the solution, thereby obtaining isolated high molecular ordered fibrilar structures.

According to more specific embodiments, in steps (a) and (b), the method of the invention requires "providing" a polypeptide (either the at least one fibrous peptide monomer or the polysaccharide binding domain, for example, CBD) and attaching both elements in step (c) to obtain a polypeptide, specifically, a chimeric polypeptide. According to one particular embodiment, preparation of each of the polypeptides provided in steps (a) and (b) may require recombinant DNA techniques that are commonly employed to perform this and are well known to those of skill in the art. Moreover, in specific embodiments, where both elements [the polypeptides provided in steps (a) and (b)], are attached or connected together by step (c), the option of fusion through the creation of a chimeric fusion protein also requires the application of recombinant DNA techniques. Typically, nucleic acid sequences encoding the different elements (i.e., fibrous protein and polysaccharide binding domain) comprised within the combined polypeptide of the invention are generated by PCR, for example by overlap extension. In this technique, the segment sequences are typically joined by incorporating the desired sequences into oligonucleotides and creating a series of products using PCR that comprise the desired segment sequences. The products may then be joined, typically using additional PCR reactions, in the proper orientation to create the fibrous protein-CBD polypeptide. The fibrous protein monomer and CBD DNA sequences may be ligated together, either directly or through a DNA sequence encoding a peptide linker, using techniques well known to those of skill in the art. These techniques include PCR as well as techniques such as in vitro ligation. The fibrous protein, that according to an illustrative non-limiting example is a spider-silk protein and CBD sequences may be linked in either orientation.

One of skill will appreciate that, utilizing the sequence information provided for the different elements used nucleic acids encoding these sequences are obtained using any number of additional methods well known to those of skill in the art. Thus, DNA encoding the fibrous protein (i.e., silk protein) is prepared by any suitable method, including, for example, other amplification techniques such as ligase chain reaction (LCR), transcription amplification and self-sustained sequence replication, or cloning and restriction of appropriate sequences. This may be converted into double stranded DNA by hybridization with a complementary sequence or by polymerization with a DNA polymerase using the single strand as a template. While it is possible to chemically synthesize an entire fibrous protein and CBD combined polypeptide, it is also possible to synthesize a number of shorter sequences (about 100 to 150 bases) that are typically later spliced together, for example using overlap extension PCR.

It should be noted that for nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Often, in order to express a protein, for example, the fibrous-protein-CBD polypeptide of the invention at high levels in a cell, codon preference for the expression system is considered in constructing the nucleic acid sequence to be expressed. Thus, a nucleic acid from one organism, e.g., a spider (for spider-silk) or a plant (for CBD) may be engineered to accommodate the codon preference of the expression system, for example, bacterial expression system.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, an expression vector typically contains a transcription unit or expression cassette that contains all the additional elements required for the expression of the protein-encoding nucleic acid in host cells. A typical expression cassette thus contains a promoter operably linked to the nucleic acid sequence encoding the protein to be expressed and signals required for efficient polyadenylation of the transcript, ribosome binding sites, and translation termination. The nucleic acid sequence encoding a protein may typically be linked to a cleavable signal peptide sequence to promote secretion of the encoded protein by the transformed cell. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences. Commonly used promoters are for example the CMV promoter, beta-lactamase (penicillinase) and lactose (lac) promoter systems, the tryptophan (trp) promoter system, the tac promoter and the lambda-derived $P_L$ promoter and N-gene ribosome binding site. The particular promoter system is not critical to the invention, any available promoter that functions in prokaryotes can be used.

It should be noted that a coding sequence and regulatory sequences are said to be "operably linked" or "operably joined" when they are covalently linked in such a way as to place the expression or transcription of the coding sequence under the influence or control of the regulatory sequences. If the regulatory sequence is positioned relative to the gene such that the regulatory sequence is able to exert a measurable effect on the amount of gene product produced, then the regulatory sequence is operably linked to the gene.

Eukaryotic expression systems for mammalian cells, yeast, and insect cells are well known in the art and are also commercially available. In yeast, vectors include Yeast Integrating plasmids (e.g., YIp5) and Yeast Replicating plasmids (the YRp series plasmids) and pGPD-2. Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include vectors allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a GPCR-encoding sequence under the direction of the polyhedrin promoter or other strong baculovirus promoters.

The elements that are typically included in expression vectors also may include a replicon that functions in $E.$ $coli$, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical any of the many resistance genes known in the art are suitable. The prokaryotic sequences are optionally chosen such that they do not interfere with the replication of the DNA in eukaryotic cells, if necessary.

Specific embodiment of the invention provides an expression vector, specifically, pET300, comprising a nucleic acid sequence encoding a spider silk-CBD fusion protein used as an non-limiting illustrative example by the method of the invention, as denoted by SEQ ID NO. 5. It should be noted that this sequence encodes a silk-CBD fusion protein containing both, S-tag and His6 tag. It should be appreciated that the invention further encompasses a nucleic acid sequence encoding the silk-CBD fusion protein with no tags, as denoted by SEQ ID NO. 15. In a further aspect, the invention provides a host cell transformed with the expression vector according to the invention.

Standard transfection methods are used to produce bacterial, mammalian, yeast or insect cell lines that express large quantities of protein, specifically, the spider silk-CBD polypeptide used by the method of the invention, which are then purified using standard techniques.

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell. It is only necessary that the particular genetic engineering procedure used be capable of successfully introducing at least one gene into the host cell capable of expressing a polypeptide of the invention.

After the expression vector is introduced into the cells, the transfected cells are cultured under conditions favoring expression of the protein, which is recovered from the culture using standard techniques identified below.

One of skill would recognize that modifications can be made to a nucleic acid encoding the silk-CBD polypeptide of the present invention without diminishing its biological activity and ability to form high molecular fibril structures. Some modifications may be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids "tags" (such as poly His or S-tag, as used herein) to aid in purification steps.

Once expressed, the polypeptide of the present invention, specifically, the silk-CBD polypeptide, can be purified according to standard procedures of the art, including but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

As mentioned above, to facilitate recovery, the expressed coding sequence can be engineered to encode the polypeptide of the present invention and fused cleavable moiety e.g. histidine. Such a fusion protein can be designed so that the polypeptide can be readily isolated by affinity chromatography; e.g., by immobilization on a column specific for the cleavable moiety.

More specifically, in a specific embodiment of the methods according to the invention, the step of isolating the polypeptide of the invention in order to provide a solution comprising the same involves purification of the protein on an affinity medium, such as for example, an affinity column, with an immobilized Ni NTA moiety as used by the present invention (see Example 1). Purification of the polypeptide on an affinity medium is preferably carried out with association to an affinity medium with an immobilized Ni NTA moiety at a pH of 7.4 followed by dissociation from the affinity medium with a desired dissociation medium comprising 0.02M sodium phosphate pH=7.4, 0.5M NaCl, 0.5M imidazole.

It is therefore understood that for purification purpose the fusion proteins of the invention may comprise at least one additional sequence, either at the amino- or the carboxy-terminus, or both, which enables ease of purification, such as, but not limited to His-tag, as used in the present invention, glutathione-S-transferase (GST), and maltose binding protein (MBP), S-tag and even CBD. Alternatively, other separation techniques may be used, such as by weight and/or size, by using a magnet, etc.

Once purified, partially or to homogeneity as desired, if to be used therapeutically, the polypeptides should be substantially free of endotoxin. More specifically, in order to provide the combined fibrous protein-CBD in a solution under conditions suitable for proper folding, the polypeptide should be obtained from biological fluids, that in this case, are bacterial extracts of transformed bacteria expressing the fusion fibrous protein-CBD polypeptide of the invention. Therefore, an active removal of lipopolysacchandes and other pyrogens from the polymers may be required. In order to obtain a protein with low pyrogenic content, which is an obligate for usage as a biomaterial in vivo and to avoid contamination by released LPS, the producing bacterial cells may be subjected to extensive washing steps.

The resulting polypeptide that is provided in a solution according to step (d) is therefore considered as pure or substantially pure. By "substantially pure" is meant substantially free from other biological molecules such as other proteins, lipids, carbohydrates, and nucleic acids. Thus, in the next step (d), a solution of said polypeptide is provided. Typically, a solution is substantially pure when at least 60%, more preferably at least 75%, even more preferably 85%, most preferably 95%, or even 99% of the protein in solution is the polypeptide of the invention, specifically, the fibrous protein- CBD polypeptide, on a wet weight or a dry weight basis. Further, a solution is substantially pure when proteins account for at least 60%, more preferably at least 75%, even more preferably 85%, most preferably 95%, or even 99% by weight of the organic molecules in solution.

As indicated herein above, applying recombinant DNA techniques, the invention uses nucleic acid sequences encoding the desired elements (i.e., spider-silk and CBD polypeptides). The terms "Nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). As appreciate by one of skill in the art, the complement of a nucleic acid sequence can readily be determined from the sequence of the other strand. Thus, any particular nucleic acid sequence set forth herein also discloses the complementary strand.

As mentioned above, the method of the invention involves the step of obtaining a polypeptide comprising an amino acid sequence of a fibrous protein monomer attached to a heterologous polysaccharide binding domain, using the recombinant DNA techniques described above, or alternative attachment procedures that will be described herein after. "Polypeptide", "peptide" and "protein" are used interchangeably herein to refer to a polymer of amino acid residues. The terms apply to naturally occurring amino acid polymers, as well as, amino acid polymers in which one or more amino acid residue is an artificial chemical mimetic of a corresponding naturally occurring amino acid.

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids. Thus, "Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. "Amino acid analogs" refers to compounds that have the same fundamental chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

Natural aromatic amino acids, Trp, Tyr and Phe, may be substituted for synthetic non-natural acid such as Phenylglycine, TIC, naphthylelanine (Nol), ring-methylated derivatives of Phe, halogenated derivatives of Phe or o-methyl-Tyr.

In addition to the above, the polypeptides of the present invention may also include one or more modified amino acids or one or more non-amino acid monomers (e.g. fatty acids, complex carbohydrates etc).

Since the present polypeptides are preferably utilized in therapeutics which requires the polypeptides to be in a soluble form, the polypeptides of the present invention may therefore include one or more non-natural or natural polar amino acids, including but not limited to serine and threonine which are capable of increasing polypeptide solubility due to their hydroxyl-containing side chain.

The polypeptides of the present invention are may be utilized in a linear form, although it will be appreciated that in cases where cyclicization does not severely interfere with polypeptide characteristics, cyclic forms of the polypeptide can also be utilized.

The polypeptides of present invention can be biochemically synthesized such as by using standard solid phase techniques. These methods include exclusive solid phase synthesis, partial solid phase synthesis methods, fragment condensation, classical solution synthesis. These methods are preferably used when the polypeptide is relatively short (i.e., 10 kDa) and/or when it cannot be produced by recombinant techniques (i.e., not encoded by a nucleic acid sequence) and therefore involves different chemistry.

Solid phase polypeptide synthesis procedures are well known in the art and further described by John Morrow Stewart and Janis Dillaha Young, Solid Phase Polypeptide Syntheses (2nd Ed., Pierce Chemical Company, 1984).

Synthetic polypeptides can be purified by preparative high performance liquid chromatography and the composition of which can be confirmed via amino acid sequencing.

As disclosed herein above in detail, recombinant techniques are preferably used to generate the polypeptides of the present invention since these techniques are better suited for generation of relatively long polypeptides (e.g., longer than 20 amino acids) and large amounts thereof. A "recombinant protein" is a manipulated form of protein, which is generated in various ways to produce large quantities of proteins, modify gene sequences and manufacture useful commercial protein quantities. Thus, the term "spider-silk-CBD fusion or chimeric protein" refers to a protein produced by an expression system having a sequence that may be based on an artificially produced nucleic acid sequence that encodes amino acid sequence of the fibrous unit of spider web proteins, combined with a nucleic acid sequence encoding CBD.

The third step (c) of the method of the invention involves attaching the fibrous protein provided in (a) to the polysaccharide binding domain provided in (b) to obtain the chimeric polypeptide of the invention. As used herein, the term "attaching" means that both polypeptides may be connected, attached, linked, fused, or combined directly or indirectly via a linker/spacer element etc., using recombinant DNA technology (as used herein). Alternatively, both polypeptides may be connected either directly or via a bridging molecule by appropriate means.

More specifically, to accomplish the objectives of the invention, a polysaccharide binding domain, specifically, CBD should be attached to a fibrous protein, i.e., spider-silk protein and therefore, an effective means for attaching both elements is necessary. Moreover, the inventors seek a controlled attachment thereof, where specific CBD will be attached or fused to specific fibrous protein in a correct orientation creating the chimeric or fusion polypeptide of the invention. In an example of such attachment, both elements may be fused either directly or via a bridging molecule, for example, a connecting spacer, linker or tether. The term "spacer" or "tether" as referred to herein, relates to a linking peptide comprising between about 2 to 5 amino acids, or about 5 to 10 amino acids, or about 10 to 15 amino acids, or about 15-30 amino acids, or about 30-50 amino acids, or about 50-70 amino acids, or about 70-90 amino acids, or about 90-150 amino acids, or about 150-300 amino acids. In particular embodiments, the spacer comprises about 5-50 amino acids.

In specific embodiments, the attachment of both elements via spacer may be followed by cross linking, such as UV cross linking.

The term "cross-linking" and "UV cross linking" as referred to herein relate to the establishment of chemical bonds that link one polymer chain, such as a polypeptide, to another that can be carried out without or with prior psoralen intercalation. For example, the cross-linking may occur directly between both elements or indirectly through bridging molecules. For UV cross-linking irradiation takes place using ultraviolet radiation in a wavelength range from 200 to 400 nm for a short time, using in particular high-pressure or medium-pressure mercury lamps with an output of from 80 to 240 W/cm. The intensity of irradiation is tailored to the particular quantum yield of the UV photoinitiator, to the degree of cross-linking which is to be established, and to establish the degree of orientation. A photoinitiator is any chemical compound that decomposes into free radicals when exposed to light. Protocols for UV cross-linking are well known in the art.

Theoretically, and according to other embodiments, both elements, the CBD and the fibrous protein may be attached via a biological affinity system. The term "biological affinity system" relates to known protein interactive partners which bind each other with high affinity and specificity and may be used as labels which facilitate the binding of molecules to which they are bound. A well known example of such a biological affinity system is the biotin-streptavidin or avidin system. Biotin is often chemically linked to nucleic acids or proteins for biochemical assays. Its small size means that its steric hindrance is usually negligible. Both streptavidin and avidin bind biotin with high affinity (kDa of ~$10^{-14}$ mol/L), and are separable only under very harsh conditions.

According to step (d), the method of the invention concerns providing a solution comprising the polypeptide of the invention. In certain embodiments, such solution is at least 1%, 5%, 10%, 15% weight/volume (w/v) fibrous protein-CBD polypeptide of the invention, i.e., silk-CBD protein. More preferably, the solution is as much as 20%, 25%, 30%, 35%, 40%, 45%, or 50% w/v fibrous protein-CBD polypeptide of the invention, i.e., silk-CBD protein. In preferred embodiments, the solution contains substantially pure fibrous protein-CBD polypeptide of the invention, i.e., silk-CBD protein. In preferred embodiments, the solution has a pH of approximately 7.5 to 5.0.

As mentioned above, in step (d) the method of the invention requires providing a solution of the combined polypeptide of the invention. By "solution" is meant any liquid mixture that contains the polypeptide of the invention that is in specific and non-limiting examples, a silk-CBD polypeptide. Such solutions may also contain, in addition to protein monomers, higher order aggregates including, for example, dimers, trimers, and tetramers of said polypeptide. The solutions are aqueous solutions, specifically, of dd$H_2O$ having a pH value suitable for the spontaneous folding or assembly and formation of the fibrilar structures of the invention. Specifically, the pH of the solution may range from about 5 to about 10, from about 5 to about 9, about 5 to about 8, about 5 to 7.5, about 5.5 to about 7.5, about 6.0 to 7.5, about 6.5 to 7.5 and about 6.5 to about 7.5. More specifically, about 7.5, 7.4, 7.3, 7.2, 7.1, 7.0, 6.9, 6.8, 6.7, 6.6 and 6.5. The skilled person is well aware of various ways of achieving this, typically involving addition of a strong or weak acid, dilution, dialysis or gel filtration. If required, this step involves both, decreasing or increasing the pH of the liquid medium to 7.5 or lower so as to allow polymerization. In a further embodiment, the solution contains less than 1% organics or chaotropic agents (w/v). Preferably, the solutions do not contain any organic solvents or chaotropic agents, yet may include additives to enhance preservation, stability, or workability of the solution. It should be noted that the solutions may be made by purifying and concentrating a biological fluid from a transgenic organism, specifically, transformed bacteria that express the recombinant polypeptide used by the method of the invention, specifically, silk-CBD. Suitable biological fluids include, for example, cell culture media (specifically, a bacterial cell culture media) or extract.

Step (e) of the method of the invention involves recovering and isolating the polypeptide of the invention, and specifically, the high molecular ordered fibrilar structures. The phrase "recovering the polypeptide or fibrilar structure" used herein refers to collecting the whole solution provided in step (d) containing the polypeptide and need not imply additional steps of separation or purification. Alternatively, the fibrilar structure generated by the method of the invention can be further purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

By recovering the resulting chimeric polypeptide, the method of the invention provides an isolated and purified fibrilar structure. As used herein, "isolated" or "substantially purified", in the context of the CBD-fibrous polypeptide or specifically, the spider silk-CBD, amino-acid sequences, as exemplified by the invention, means the amino-acid sequences have been removed from their natural milieu or have been altered from their natural state. As such "isolated" does not necessarily reflect the extent to which the amino-acid sequences have been purified. However, it will be understood that such molecules that have been purified to some degree are "isolated". If said molecules do not exist in a natural milieu, i.e. it does not exist in nature, the molecule is "isolated" regardless of where it is present.

Furthermore, the term "isolated" or "substantially purified", when applied to an amino acid sequence, denotes that the amino acid sequence or nucleic acid is essentially free of other cellular components with which they are associated in the natural state. It is preferably in a homogeneous state, although it can be in either a dry or aqueous solution. Purity and homogeneity are typically determined using analytical chemistry techniques such as polyacrylamide gel electrophoresis or high performance liquid chromatography. An amino acid sequence which is the predominant species present in a preparation is substantially purified.

In another embodiment, the method of the invention further comprising the step of sonicating the solution of said isolated polypeptide obtained in (d) under conditions which allow folding of the fibrous protein-CBD chimera to generate said fibrilar structures. By sonication it means applying ultrasound energy to the solution, for agitating particles therein. Said sonication may be performed by using an ultrasonic bath or an ultrasonic probe (i.e. a sonicator). According to the method of the invention, sonication may be performed on a solution having a polypeptide concentration of from about 0.1 mg/ml to about 200 mg/ml, from about 1 mg/ml to about 200 mg/ml, about 10 mg/ml to about 200 mg/ml, about 20 mg/ml to about 200 mg/ml, about 30 mg/ml to about 200 mg/ml, about 40 mg/ml to about 200 mg/ml, about 50 mg/ml to about 200 mg/ml, or from about 60 mg/ml to about 80 mg/ml. Specifically, about 20 mg/ml to about 200 mg/ml. The sonication of the method of the invention may be performed for at least 1, 2, 3 or more cycles, wherein each cycle consists of from 1 to 5 pulse-discharges of about 5 kHz to about 50 kHz, about 10 kHz to about 30 kHz, or about 20 kHz, for a time period of from about 1 sec. to about 10 min. In a specific embodiment, the sonication may be performed once for about 2 min.

In some specific embodiments, the method of the invention further comprising the step of concentrating the solution of said isolated polypeptide obtained in (d) prior to, after, or instead of, the sonication step. More specifically, the solution may be concentrated before sonication. The concentration step may be performed by using any known method, e.g. affinity chromatography, dialysis using membranes with known MWCO, etc. The final concentration of the solution of said isolated polypeptide, may be from about 0.1 mg/ml to about 500 mg/ml, from about 1.0 mg/ml to about 250 mg/ml, from about 10 mg/ml to about 150/ml, or from about 50 mg/ml to about 100 mg/ml. Specific embodiment relate to a concentration of about 40 mg/ml to about 100 mg/ml or about 60 mg/ml.

According to one specific embodiment, concentration of the solution may be performed using Centrocon with a MWCO (Molecular Wight cutoff) of 10 kDa, as used in the present invention.

As mentioned, the isolated polypeptides of the present invention comprise a monomer of a fibrous polypeptide attached to a heterologous polysaccharide binding domain.

As used herein, the qualifier "heterologous" when relating to the heterologous polysaccharide binding domains of the fibrous polypeptides of the present invention indicates that the heterologous polysaccharide binding domain is not naturally found in that fibrous polypeptide to which it is fused.

The phrase "polysaccharide binding domain" refers to an amino acid sequence which binds a polysaccharide with a minimal dissociation constant (kDa) of about 10 µM. Typically, the polysaccharide binding domain comprises at least a functional portion of a polysaccharide binding domain of a polysaccharidase or a polysaccharide binding protein.

It will be appreciated that exemplary polysaccharide binding domains include but are not limited to a cellulose binding domain (specific example of which is set forth in SEQ ID NO. 4), chitin binding domain, a starch binding domain, a dextran binding domain, a glucan binding domain, a chitosan binding domain, an alginate binding domain and an hyaluronic acid binding domain.

More specifically, exemplary sources of polysaccharide binding domains which are contemplated for use in the present invention include, but are not limited to: Cellulose Binding Domains from any one of β-glucanases (avicelases, CMCases, cellodextrinases), exoglucanases or cellobiohydrolases, cellulose binding proteins, xylanases, mixed xylanases/glucanases, esterases, chitinases, β-1,3-glucanases, β-1,3-(β-1,4)-glucanases, (β-)mannanases, β-glucosidases/galactosidases cellulose synthases (unconfirmed); Starch/Maltodextrin Binding Domains from any one of α-amylases, β-amylases, pullulanases, glucoamylases, cyclodextrin glucotransferases (cyclomaltodextrin glucanotransferases), maltodextrin binding proteins; Dextran Binding Domains from any one of (Streptococcal) glycosyl transferases, dextran sucrases (unconfirmed), Clostridial toxins, glucoamylases, dextran binding proteins; β-Glucan Binding Domains from any one of β-1,3-glucanases, β-1,3-(β-1,4)-glucanases (unconfirmed), β-1,3-glucan binding protein; Chitin Binding Domains from any one of chitinases, chitobiases, chitin binding proteins and Heivein.

According to specific embodiment of the invention the polysaccharide binding domain used for the method of the invention is a cellulose binding domain (CBD).

In another specific embodiment, the CBD used by the method of the invention may be CBDclos. According to more specific embodiments, the CBDclos used by the method of the invention comprises the amino acid sequence as denoted by SEQ ID NO. 4, or any homologues, variants and derivatives thereof.

The present invention is the first to utilize CBD's ability to form dimers or higher molecular weight compounds in order to enable assembly of CBD fusion proteins and formation of higher molecular fibrilar structures. The present invention is the first to demonstrate CBD's ability to spontaneously create higher hierarchy ordering by presenting its fusion to dragline spider silk proteins. As used herein, the phrase "fibrous polypeptide" refers to a polypeptide that consists of a plurality of monomer chains arranged in a matrix so as to form fibers or sheets.

Therefore, according to one embodiment, the fibrous polypeptide used for the method of the invention may be any one of spider-silk, resilin, elastin, silk-worm silk, collagen and mussel byssus protein.

As used herein, the term "spider silk" refers to a polypeptide capable of forming a fiber which is comprised of spider silk, wherein each monomer thereof comprises at least two repeating units of the sequence set forth in SEQ ID NO: 14. It should be appreciated that the invention further encompasses an amino acid sequence of the silk polypeptide containing both, S-tag and His$_6$ tag as denoted by SEQ ID NO. 2. According to one embodiment, the polypeptide chain comprises a spidroin 1 amino acid sequence. According to another embodiment, the polypeptide chain comprises a spidroin 2 amino acid sequence. According to one embodiment, the spider silk is dragline spider silk. GenBank Accession Nos. of non-limiting examples of spidroins 1 and 2 include the following NCBI sequence numbers: P19837 (Spidroin 1), AAC38957 (Spidroin 1), ABR68858 (Spidroin 2), AAT75317 (Spidroin 2) and P46804 (Spidroin 2).

It should be appreciated that a spider silk polypeptide of the present invention also refers to homologues (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to spider silk sequences listed above as determined using BlastP software of the National Center of Biotechnology Information (NCBI) using default parameters). As will be explained in detail herein after, the homolog may also refer to a deletion, insertion, or substitution variant, including an amino acid substitution, thereof and biologically active polypeptide fragments thereof.

As used herein, the term "silkworm silk" refers to a silk polypeptide derived from silkworm, capable of forming a fiber. GenBank Accession Nos. of non-limiting examples of silkworm silk polypeptides include: AAL83649, AAA27839, NP001106733, NP001037488 and Caa35180.

As used herein, the term "resilin" refers to an elastic polypeptide, capable of forming a fiber. GenBank Accession Nos. of non-limiting examples of resilin includes the following NCBI sequence numbers: NP 995860 (*Drosophila melanogaster*), NP 611157 (*Drosophila melanogaster*), Q9V7U0 (*Drosophila melanogaster*), AAS64829, AAF57953 (*Drosophila melanogaster*), XP 001817028 (*Tribolium castaneum*) and XP001947408 (*Acyrthosiphon pisum*).

As used herein, the term "elastin" refers to an elastic polypeptide, capable of forming a fiber. GenBank Accession Nos. of non-limiting examples of elastin include the following NCBI sequence numbers: NP786966 (*Bos taurus*), NP 031951 (mouse), NP 036854 (rat), AAC98395 (human) and I47076 (seep).

As used herein, the term "collagen" refers to an assembled collagen trimer, which in the case of type I collagen includes two alpha 1 chains and one alpha 2 chain. A collagen fiber is collagen which is devoid of terminal propeptides C and N. Contemplated collagens include types I, II, III, V, XI, and biologically active fragments therefrom. The collagen may be comprised of procollagen, atelocollagen or telocollagen. GenBank Accession Nos. of non-limiting examples of collagen include: P02452 and P08123.

As used herein, the phrase "mussel byssus protein" refers to the polypeptide found in the byssal threads of mussels comprising both collagen and elastin domains (e.g. Col-P or Col-D). NCBI sequence numbers include AAB34042.

Due to its physical and chemical properties, spider silk is a sought-after material, and many attempts were made to produce it in commercial quantities. Spider silk is a remarkably strong material. Its tensile strength is comparable to that of high-grade steel (1500 MPa), and about half as strong as aramid filaments, such as Twaron or Kevlar (3000 MPa). Spider silk is about a fifth of the density of steel; a strand long enough to circle the Earth would weigh less than 500 grams (18 oz). Spider silk is also especially ductile, able to stretch up to 1.4 times its relaxed length without breaking. It can hold its strength below −40° C.

Many species of spider have different glands to produce silk with different properties for different purposes, including housing, web construction, defense, capturing and detaining prey, egg protection, and mobility. Different specialized silks have evolved with properties suitable for different uses. For example, *Argiope argentata* has five different types of silk, each used for a different purpose: dragline silk is used for the web outer rim and spokes and the lifeline. It is as strong per unit weight as steel, but much tougher. Capture-spiral silk is used for the capturing lines of the web. It is sticky, extremely stretchy and tough. Tubiliform silk is used for protective egg sacs. It is the stiffest silk. Aciniform silk is used to wrap and secure freshly captured prey. It is two to three times as tough as the other silks, including dragline. Finally, minor-ampullate silk is used for temporary scaffolding during web construction.

Although different species of spiders and different types of silk have different protein sequences, a general trend in spider silk structure is a sequence of amino acids (usually alternating glycine and alanine, or alanine alone) that self-assemble into a beta sheet conformation. These "Ala rich" blocks are separated by segments of amino acids with bulky side-groups. The beta sheets stack to form crystals, whereas the other segments form amorphous domains.

It is the interplay between the hard crystalline segments, and the strained elastic semi amorphous regions that gives spider silk its extraordinary properties. The high toughness is due to the breaking of hydrogen bonds in these regions.

Spider silk is as strong as many industrial fibers, stronger than many and tougher than all, and so there is commercial interest in duplicating spider silk artificially, since spiders use renewable materials as input and operate at room temperature, low pressures and using water as a solvent. However, it has been difficult to find a commercially viable process to mass-produce spider silk. The method of the invention specifically demonstrated the generation of high molecular ordered fibrilar structures of spider silk protein using CBD for inducing proper self assembly and folding.

Thus, according to a specific embodiment, the fibrous protein that may be used for the method of the invention is a spider silk protein. As shown by the experimental procedures section, a 15-mer unit of *Nephila clavipes* was used as the spider silk protein. It is therefore appreciated that certain specific embodiments of the invention concerns the use of a spider-silk monomer comprising the amino acid sequence as denoted by SEQ ID NO. 14, or any homologues, variants or derivatives thereof. It should be appreciated that the invention further encompasses an amino acid sequence of the silk polypeptide with tags (His6 and S-tag), as denoted by SEQ ID NO. 2.

It is appreciated that while the invention generally relates to chimeric CBD-spider silk proteins or any fragments or parts thereof derived from *Nephila clavipes*, dragline silk, many other spider species may be used to derive synthetic spider silk in a similar manner. More preferably, the dragline proteins are derived from one or more of the following spiders: *Araneus diadematus, Arachnura higginsi, Araneus circulissparsus, Araneus diadematus, Argiope picta*, Banded Garden Spider (*Argiope trifasciata*), Batik Golden Web Spider (*Nephila antipodiana*), Beccari's Tent Spider (*Cyrtophora beccarii*), Bird-dropping Spider (*Celaenia excavata*), Black-and-White Spiny Spider (*Gasteracantha kuhlii*), Black-and-yellow Garden Spider (*Argiope aurantia*), Bolas Spider (*Ordgarius furcatus*), Bolas Spiders Magnificent Spider (*Ordgarius magnificus*), Brown Sailor Spider (*Neoscona nautica*), Brown-Legged Spider (*Neoscona rufofemorata*), Capped Black-Headed Spider (*Zygiella calyptrata*), Common Garden Spider (*Parawixia dehaani*), Common Orb Weaver (*Neoscona oxancensis*), Crab-like Spiny Orb Weaver (*Gasteracantha cancriformis* (elipsoides)), Curved Spiny Spider (*Gasteracantha arcuata*), *Cyrtophora moluccensis, Cyrtophora parnasia, Dolophones conifera, Dolophones turrigera*, Doria's Spiny Spider (*Gasteracantha doriae*), Double-Spotted Spiny Spider (*Gasteracantha mammosa*), Double-Tailed Tent Spider (*Cyrtophora exanthematica*), *Aculeperia ceropegia, Eriophora pustulosa*, Flat Anepsion (*Anepsion depressium*), Four-spined Jewel Spider (*Gasteracantha quadrispinosa*), Garden Orb Web Spider (*Eriophora transmarina*), Giant Lichen Orbweaver (*Araneus bicentenarius*), Golden Web Spider (*Nephila maculata*), Hasselt's Spiny Spider (*Gasteracantha hasseltii*), *Tegenaria atrica, Heurodes turrita*, Island Cyclosa Spider (*Cyclosa insulana*), Jewel or Spiny Spider (*Astracantha minax*), Kidney Garden Spider (*Araneus mitificus*), Laglaise's Garden Spider (*Eriovixia laglaisei*), Long-Bellied Cyclosa Spider (*Cyclosa bifida*), Malabar Spider (*Nephilengys malabarensis*), Multi-Coloured St Andrew's Cross Spider (*Argiope versicolor*), Ornamental Tree-Trunk Spider (*Herennia ornatissima*), Oval St. Andrew's Cross Spider (*Argiope aemula*), Red Tent Spider (*Cyrtophora unicolor*), Russian Tent Spider (*Cyrtophora hirta*), Saint Andrew's Cross Spider (*Argiope keyserlingi*), Scarlet Acusilas (*Acusilas coccineus*), Silver Argiope (*Argiope argentata*), Spinybacked Orbweaver (*Gasteracantha*

*cancriformis*), Spotted Orbweaver (*Neoscona domiciliorum*), St. Andrews Cross (*Argiope aetheria*), St. Andrew's Cross Spider (*Argiope Keyserlingi*), Tree-Stump Spider (*Poltys illepidus*), Triangular Spider (*Arkys clavatus*), Triangular Spider (*Arkys lancearius*), Two-spined Spider (*Poecilopachys australasia*), other *Nephila* species, e.g. *Nephila senegalensis, Nephila madagascariensis* and many more. Most preferred, the dragline proteins provided by the invention are the *Nephila clavipes* proteins.

It should be appreciated that a polypeptide combining spider-silk-CBD used by the method of the invention to generate the high molecular fibril structures is disclosed herein only as a non-limiting illustrative example. Such polypeptide has an amino acid sequence as denoted by SEQ ID NO. 6. In yet another embodiment, the invention encompasses spider-silk-CBD polypeptide with no tags (S-tag and His6 tag) as denoted by the amino acid sequence of SEQ ID NO. 16. It should be appreciated that the invention further contemplates any polypeptide having a similar, homologue or variant amino acid sequence as well.

An amino acid sequence (peptide) or a nucleic acid is said to be a homolog of a corresponding amino acid sequence, peptide or a nucleic acid, when the homology is determined to be at least about 50%, at least about 55%, at least about 60%, at least about 65%, at least about 70%, at least about 75%, at least about 80%, at least about 85%, at least about 90%, at least about 92%, at least about 94%, at least about 96%, at least about 98% or at least about 99%.

Homology, as used herein, may be determined on the basis of percentage identity between two amino acid (peptide) or DNA sequences. In general, the two sequences to be compared are aligned to give a maximum correlation between the sequences. The alignment of the two sequences is examined and the number of positions giving an exact amino acid (or nucleotide) correspondence between the two sequences determined, divided by the total length of the alignment multiplied by 100 to give a percentage identity figure. This percentage identity figure may be determined over the whole length of the sequences to be compared, which is particularly suitable for sequences of the same or very similar lengths and which are highly homologous, or over shorter defined lengths, which is more suitable for sequences of unequal length or which have a lower level of homology. Methods for comparing the identity of two or more sequences are well known in the art. Thus for instance, programs available in the Wisconsin Sequence Analysis Package, version 9.1, for example the programs GAP and BESTFIT, may be used to determine the percentage identity between two amino acid sequences and the percentage identity between two polynucleotides sequences. BESTFIT uses the "local homology" algorithm of Smith and Waterman and finds the best single region of similarity between two sequences. BESTFIT is more suited to comparing two polypeptide or two polynucleotide sequences which are dissimilar in length, the program assuming that the shorter sequence represents a portion of the longer. In comparison, GAP aligns two sequences finding a "maximum similarity" according to the algorithm of Needleman and Wunsch. GAP is more suited to comparing sequences which are approximately the same length and an alignment is expected over the entire length. Preferably the parameters "Gap Weight" and "Length Weight" used in each program are 50 and 3 for polynucleotide sequences and 12 and 4 for polypeptide sequences, respectively. Preferably, percentage identities and similarities are determined when the two sequences being compared are optimally aligned.

The terms "identical", "substantial identity", "substantial homology" or percent "identity", in the context of two or more amino acids or nucleic acids sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., amino acid sequence SEQ ID NO:2, 14, 4, 6 and 16), when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical". This definition also refers to, or may be applied to, the compliment of a test sequence. The definition also includes sequences that have deletions and/or additions, as well as those that have substitutions. The preferred algorithms can account for gaps and the like. More specifically, said identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

It should be appreciated that the invention further encompasses a polypeptide comprising the amino acid sequence of SEQ ID NO. 6, or any variants thereof. In yet another embodiment, the invention provides a spider-silk-CBD polypeptide with no tags as denoted by the amino acid sequence of SEQ ID NO. 16. As used herein, the term "variant" or "substantially similar" comprises sequences of amino acids or nucleotides different from the specifically identified sequences, in which one or more, specifically, between 1 to 50, more specifically, 1, 2, 3, 4, 5, 6, 7, 8, 9, 10, 20, 30, 40 or 50, amino acid residues or nucleotides are deleted, substituted or added. The variants may be allelic variants occurring naturally or variants of non-natural origin. The variant or substantially similar sequences refer to fragments of amino acid sequences or nucleic acids that may be characterized by the percentage of the identity of their amino acid or nucleotide sequences with the amino acid or nucleotide sequences described herein, as determined by common algorithms used in the state-of-the-art. The preferred fragments of amino acids or nucleic acids are those having a sequence of amino acids or nucleotides with at least around 40 or 45% of sequence identity, preferentially around 50% or 55% of sequence identity, more preferentially around 60% or 65% of sequence identity, more preferentially around 70% or 75% of sequence identity, more preferentially around 80% or 85% of sequence identity, yet more preferentially around 90%, 91%, 92%, 93%, 94%, 95%, 96%, 97%, 98% or 99% of sequence identity when compared to the sequence of reference.

According to other embodiments, the variants in each case comprise between 1 to 10, specifically, 1, 2, 3, 4, 5, 6, 7, 8, 9, or 10 amino acid substitutions, deletions, insertions, and/or additions, which do not disturb the proper assembly of the polypeptide of the invention into a high molecular ordered fibrilar structure, and do not negatively affect tensile strength and elasticity of a thread formed from a recombinant protein comprising said amino acid sequence.

"Insertions" or "deletions" are typically in the range of about 1 to 10 amino acids, specifically, 1, 2, 3, 4, 5, 6, 7, 8, 9, or 10. More specifically, insertions or deletions of about 1, 2 or 3 amino acids. Amino acid additions typically are not more than 100, more specifically not more than 80, more specifically not more than 50, most specifically not more than 20 amino acids, which are added on and/or inserted into the proteins of the present invention. It is noted that only those additions are contemplated in this invention, which do not disturb the proper assembly of the polypeptide of the invention into a high molecular ordered fibrilar structure, and do not negatively affect tensile strength and elasticity of a thread formed from said fibrilar structure.

It should be noted that "insertions" or "additions" of amino acid residues include incorporation of additional residues within the amino acid sequence of the invention. Additionally or alternatively, these terms encompass the amino acid sequence of the invention that is extended at the N-terminus and/or C-terminus thereof with various identical or different amino acid residues.

Amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

With respect to amino acid sequences, one of skill will recognize that individual substitutions, deletions or additions to an amino acid, nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologues, and alleles of the invention.

For example, substitutions may be made wherein an aliphatic amino acid (G, A, I, L, or V) is substituted with another member of the group, or substitution such as the substitution of one polar residue for another, such as arginine for lysine, glutamic for aspartic acid, or glutamine for asparagine. Each of the following eight groups contains other exemplary amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M).

Conservative nucleic acid substitutions are nucleic acid substitutions resulting in conservative amino acid substitutions as defined above.

Variants of the amino acid sequences of the invention may have at least 80% sequence similarity, often at least 85% sequence similarity, 90% sequence similarity, or at least 95%, 96%, 97%, 98%, or 99% sequence similarity at the amino acid level, with the synthetic repetitive units of the spider silk protein of the invention, specifically, the polypeptide as denoted by SEQ ID NO. 6 or by SEQ ID NO. 16.

The spider silk-CBD chimeric polypeptide of the invention may comprise the amino acid sequence of SEQ ID NO. 6, SEQ ID NO. 16, or of any fragment thereof A "fragment" constitutes a fraction of the amino acid sequence of a particular region. A fragment of the peptide sequence is at least one amino acid shorter than the particular region. The fragment may be truncated at the C-terminal or N-terminal sides, or both.

Mutants of the amino acid sequences of the invention are characterized in the exchange of one (point mutant) or more, about up to 10, of its amino acids against one or more of another amino acid. They are the consequence of the corresponding mutations at the DNA level leading to different codons.

Still further, the invention concerns derivatives of the amino acid sequence of the invention. Derivatives of the amino acid sequences of the invention are, for example, where functional groups, such as amino, hydroxyl, mercapto or carboxyl groups, are derivatized, e.g. glycosylated, acylated, amidated or esterified, respectively. In glycosylated derivatives an oligosaccharide is usually linked to asparagine, serine, threonine and/or lysine. Acylated derivatives are especially acylated by a naturally occurring organic or inorganic acid, e.g. acetic acid, phosphoric acid or sulphuric acid, which usually takes place at the N-terminal amino group, or at hydroxy groups, especially of tyrosine or serine, respectively. Esters are those of naturally occurring alcohols, e.g. methanol or ethanol. Further derivatives are salts, especially pharmaceutically acceptable salts, for example metal salts, such as alkali metal and alkaline earth metal salts, e.g. sodium, potassium, magnesium, calcium or zinc salts, or ammonium salts formed with ammonia or a suitable organic amine, such as a lower alkylamine, e.g. triethylamine, hydroxy-lower alkylamine, e.g. 2-hydroxyethylamine, and the like.

It should be recognized that the chimeric spider silk-CBD polypeptide of SEQ ID NO. 6 is used herein only as a non-limiting illustrative example demonstrating the feasibility of using CBD for induction of proper assembly of fibrous proteins. This particular polypeptide, comprises for purification purposes a tag, specifically, a $His_6$ tag. It should be understood that the invention encompasses the use of any appropriate tag facilitating isolation of the polypeptide. The term "tag", as used herein, refers to a molecule that can be attached to a larger macromolecule, and which can be used to separate that macromolecule from macromolecules that do not have the tag, or facilitate the specific visualization of said macromolecule. More specifically, the tag referred to herein are protein tags, which consist of specific amino acid sequences that are recognized and bound by known ligands.

It is understood that, where appropriate, when adding an N-terminal or a C-terminal tag, or both to a polypeptide, as exemplified by SEQ ID NO. 6, the polypeptide initial methionine encoded by the initiation codon (ATG) may be re-located to the N-terminus of said tag, to facilitate translation initiation.

In some embodiments, the amino acid sequence according to the invention comprises an N-terminal and C-terminal tag sequence, the tag sequence being the $His_6$-containing sequence HHHHHH, also denoted as SEQ ID NO.: 9. It should be noted that in some embodiments, a DNA sequence encoding HHHHHH may be CACCATCATCATCATCAT-CAT, as denoted by SEQ ID NO. 10, as used for the N-terminal tag, and the sequence CACCACCACCACCACCAC, as denoted by SEQ ID NO. 11, as used for the C-terminal tag. It should be noted that another tag has been used for the invention, S-tag, MKETAAAKFERQHMDS, as denoted by SEQ ID NO. 12. Further tag sequences include HA-tag, Glutathione-S-transferase tag, Maltose-Binding-Protein tag and even CBD can serve as a tag for purification on cellulose.

As shown by the following Examples 3, 4 and 5, the high molecular ordered fibrilar structures generated by the method of the invention have been characterized using different techniques establishing their structural properties.

Thus, according to one embodiment, the fibrilar structure generated by the method of the invention is composed of several monomers. Each silk-CBD monomer is about 50 kDa to 100 kDa or higher in size, specifically, about 65 kDa or higher. Because of their structure, it is known that silk proteins often run with higher molecular weight than expected in gel filtration. As shown by the gel filtration data presented in Example 2, the silk-CBD monomer or dimer has a molecular weight of about 230 kDa. The proteins eluted in the void volume represent oligomers of the silk-CBD protein that are the fibrilar structures of the invention. Therefore, the fibrilar structure of the invention may be characterized by at least one of a molecular weight of about 230 kDa or higher, or specifically, about 250 kDa or higher, about 500 kDa or higher, about 1000 kDa or higher, about 10,000 kDa or higher, about 30,000 kDa or higher, about 50,000 kDa or higher, about 100.000 kDa or higher, about 200,000 kDa or higher, or about 250,000 kDa or higher.

As shown by Example 3, the diameter of the fibrilar structures generated by the method of the invention was analyzed using DLS (dynamic light scattering). Thus, in yet another embodiment, the fibrilar structures generated by the method of the invention is further characterized as having a diameter of between about 50 nm to about 2500 nm or higher, 100 nm to about 2100 nm or higher, or 150 nm to about 1500 nm or higher. More specifically, a solution containing said fibrilar structures mostly contains large fibrilar structures having a diameter of about 2100 nm or higher. By using the term "mostly contains" it is meant that about 30-95% of the structures in the solution having a diameter of about 2100 nm or higher, specifically, about 30%, 35%, 40%, 45%, 50%, 55%, 60%, 65%, 70%, 75%, 80%, 85%, 90%, 95% and more.

Still further, according to another embodiment, the fibrilar structures generated by the method of the invention display a length of about 100 to about 2000 nm or higher. More specifically, the length of the fibrilar structures generated by the invention may range, for example, nanofibrils are in the range of 1-10 nm, the nanofibrils form micelles in the range of 10-100 nm, which forms liquid crystalline structures of about 500-1000 nm. Fibers and webs are in a length of about 10 μm or higher.

Preferred fibrilar structures may include different polymer shapes such as a fiber, film, foam, net or mesh. In certain embodiments, it is preferable that the fibrilar structure generated by the method of the invention is a fiber with a macroscopic size, i.e. with a diameter above 0.1 μm, preferably above 1 μm, and a length above 5 mm. It is preferred that the fiber has a diameter in the range of 1-400 μm, preferably 60-120 and a length in the range of 0.5-300 cm, preferably 1-100 cm. Other preferred ranges are 0.5-30 cm and 1-20 cm. It is also preferred that the fibrilar structure, such as a fiber, according to the invention has a tensile strength above 1 MPa, preferably above 2 MPa, more preferably 10 MPa or higher. It is preferred that the polymer, such as a fiber, of the spider silk-CBD polypeptide according to the invention has a tensile strength above 100 MPa, more preferably 200 MPa or higher. The fiber has the capacity to remain intact during physical manipulation, i.e. can be used for spinning, weaving, twisting, crocheting and similar procedures. "Spinning" refers to the process of making filament or fiber by extrusion of a fiber forming substance, drawing, twisting, or winding fibrous substances.

Example 4 demonstrates X-ray scattering analysis performed in order to further characterize the structural properties of the fibrilar structures of the invention. In a specific embodiment, the fibrilar structure generated by the method of the invention is arranged in a lattice comprising at least two subunits along an "a" axis and at least two subunits along a "b" axis, and wherein the angle (γ) between at least two adjacent polypeptides is between about 70° to about 120° or higher, between about 80° to about 110° or higher, between about 90° to about 100° or higher and between about 80° to about 95° or higher. It should be noted that the angle is changing as the solution is more concentrated or the sonication conditions favor folding and self assembly of said structures. More specifically, the rate of such change in the angle may range from about 5% to about 95%, specifically, 5%, 10%, 15%, 20%, 25%, 0%, 35%, 40%, 45%, 50%, 55%, 60%, 65%, 70%, 75%, 80%, 85%, 90% and 95% and more.

As more as the solution contains self-assembled fibrilar structures, the distance from the center of one subunit to the other shortens. Thus, in another embodiment, the distance between at least two subunits along an "a" axis is between about 10 to about 70 nm or lower, between about 20 to about 60 nm or lower, between about 30 to about 50 nm or lower, or between about 30 to about 35 nm or lower. The distance between at least two subunits along a "b" axis is between about 10 to about 70 nm or lower, between about 20 to about 60 nm or lower, between about 30 to about 50 nm or lower or between about 40 to about 55 nm or lower.

Recombinant fibrous proteins, and especially silk proteins, are abundant. However, converting them into a final fibrilar structure is extremely difficult and highly complicated. Accordingly, in a further aspect the invention provides an isolated high molecular ordered fibrilar structure consisting of at least one isolated polypeptide comprising an amino acid sequence of fibrous protein monomer attached to a heterologous polysaccharide binding domain.

In one specific embodiment, the polysaccharide binding domain comprised within the fibrilar structure of the invention may be any one of a cellulose binding domain (CBD), a chitin binding domain, a starch binding domain, a dextran binding domain, a glucan binding domain, a chitosan binding domain, an alginate binding domain and an hyaluronic acid binding domain. According to one specific embodiment, the polysaccharide binding domain is a cellulose binding domain (CBD). In a more specific embodiment, the CBD is CBDclos. More specifically, such CBDclos comprises the amino acid sequence as denoted by SEQ ID NO. 4 or any homologues, derivatives and variants thereof.

In another embodiment, the fibrous polypeptide comprised within the isolated fibrilar structure of the invention may be any one of spider-silk, resilin, elastin, silk-worm silk, collagen and mussel byssus protein.

Specifically, the fibrilar structures of the invention are composed of a spider-silk monomer. In more specific embodiments, the spider silk protein comprises the amino acid sequence as denoted by SEQ ID NO. 14, or any homologues, variants or derivatives thereof. The invention further provides a 15-mer of silk protein with S-tag and the His6 tag, as denoted y SEQ ID NO. 2. Taken together, according to certain specific embodiments, the fibrilar structure of the invention is composed of a spider-silk-CBD chimeric polypeptide. In more specific embodiments, such spider-silk-CBD polypeptide comprises the amino acid sequence as denoted by SEQ ID NO. 16, or any homologues, variants or derivatives thereof. In yet another embodiment, the invention encompasses spider-silk-CBD polypeptide with S-tag and the His6 tag as denoted by the amino acid sequence of SEQ ID NO. 6.

In another specific embodiment the fibrilar structures of the invention is further characterized as having a diameter of between about 50 nm to about 2500 nm or higher, 100 nm to about 2100 nm or higher, or 150 nm to about 1500 nm or higher. More specifically, a solution containing said fibrilar structures mostly contains large fibrilar structures having a diameter of about 2100 nm or higher. More specifically, about 30-95% of the structures in the solution having a diameter of about 2100 nm or higher, specifically, about 30%, 35%, 40%, 45%, 50%, 55%, 60%, 65%, 70%, 75%, 80%, 85%, 90%, 95% and more.

Still further, according to another embodiment, the fibrilar structures of the invention display a length of about 100 to about 2000 nm or higher. More specifically, the length of the fibrilar structures generated by the invention may range, for example, nanofibrils are in the range of 1-10 nm in length, the nanofibrils form micelles in the range of 10-100 nm in length, which forms liquid crystalline structures of about 500-1000 nm. Fibers and webs are about 10 µm or higher, in length.

In a specific embodiment, the fibrilar structure of the invention is arranged in a lattice comprising at least two subunits along an "a" axis and at least two subunits along a "b" axis, and wherein the angle (γ) between at least two adjacent polypeptides is between about 70° to about 120° or higher, between about 80° to about 110° or higher, between about 90° to about 100° or higher and between about 80° to about 95° or higher. It should be noted that the angle is changing as the solution is more concentrated or the sonication conditions favor folding and self assembly of said structures. More specifically, the rate of such change in the angle may range from about 5% to about 95%, specifically, 5%, 10%, 15%, 20%, 25%, 30%, 35%, 40%, 45%, 50%, 55%, 60%, 65%, 70%, 75%, 80%, 85%, 90% and 95% and more. In another embodiment, the distance between at least two subunits along an "a" axis is between about 10 to about 70 nm or lower, between about 20 to about 60 nm or lower, between about 30 to about 50 nm or lower, or between about 30 to about 35 nm or lower. The distance between at least two subunits along a "b" axis is between about 10 to about 70 nm or lower, between about 20 to about 60 nm or lower, between about 30 to about 50 nm or lower or between about 40 to about 55 nm or lower.

In a specific embodiment, high molecular ordered fibrilar structure of the invention may be a fiber, film, foam, net or mesh. Moreover, the isolated fibrilar structure can be cast into a mold to form hydrogels, sponges, films, foams etc' and can be extruded to form fibers.

The term "fibrilar structure" or "fiber structure" according to the invention refers to any 2D and/or 3D structure formed by assembling fibers, or allowing the assembly of fibers, prepared according to the method of the invention. According to one embodiment, the invention provides fiber structure(s) in the form of "layers of fibers", for example a thin film. In particular, the thin film may have the thickness of one fiber. Even more in particular, the thin film may have a thickness equivalent or substantially equivalent to the diameter of one fiber. The layer of fibers or thin film may also be modified to prepare a scaffold or 3D fiber structure. It is to be understood that the fibrilar structure of the invention may be, but not limited to, a fiber, a film, a net, grid or mesh, a foam, a hydrogel, a sponge, spheres, nanofibrils, or a scaffold. According to one specific embodiment, the isolated fibrilar structure of the invention is a fiber.

Thus, in a further aspect, the present invention relates to a fiber consisting of at least one isolated polypeptide comprising an amino acid sequence of fibrous protein monomer attached to a heterologous polysaccharide binding domain. In specific embodiments, the fiber of the invention is composed of a spider silk-CBD chimeric polypeptide. According to specific and particular embodiments, the fiber provided by the invention is composed of a spider silk-CBD chimeric polypeptide comprising the amino acid sequence as denoted by SEQ ID NO. 16 or any homologues, variants and derivatives thereof. In yet another embodiment, the invention encompasses spider-silk-CBD polypeptide with tags as denoted by the amino acid sequence of SEQ ID NO. 6.

"Fiber" as used herein refers to at least one fiber prepared according to any embodiment of the invention. The fiber may have a diameter of about 300 µm or less, about 100 µm or less, about 10 µm or less, about 1000 nm or less, about 500 nm or less, about 300 nm or less, about 100 nm or less, about 50 nm or less, about 30 nm or less, about 10 nm or less. The term "fiber" encompasses "nanofiber". The fiber according to the invention may also be referred to as nano-fiber, thereby indicating that the fibers may either have a diameter in the pm range or in the nm range. For the purpose of the present invention, the term "nanofiber" is used to refer to a fiber having a diameter of about 10000 nm (10 µm) or less. More specifically, nanofibrils are in the range of 1-10 nm, these nanofibrils may form micelles in the range of 10-100 nm, which forms liquid crystalline structures of about 500-1000 nm. Fibers and webs are 10 µm or more, in length.

It should be appreciated that the fibrilar structures generated by the methods of the invention display different structural properties including tensile strength, and elasticity that are similar to native bio fibers. "Tenacity" or "tensile strength" refers to the amount of weight a filament can bear before breaking. The maximum specific stress that is developed is usually in the filament, yarn or fabric by a tensile test to break the materials. According to specific embodiments, the fiber of the invention has tensile strength of about 100-3000 MPa (MPa=N/mm$^2$).

"Toughness" refers to the energy needed to break the fiber. This is the area under the force elongation curve, sometimes referred to as "energy to break" or work to rupture. According to particular embodiments, the fiber of the invention a toughness of about 20-1000 MJ/m$^3$, about 50-950 MJ/m$^3$, about 100-900 MJ/m$^3$, about 120-850 MJ/m$^3$, about 150-800 MJ/m$^3$, about 180-700 MJ/m$^3$, about 180-750 MJ/m$^3$, about 250-700 MJ/m$^3$, about 280-600 MJ/m$^3$, about 300-580 MJ/m$^3$, about 310-560 MJ/m$^3$, about 320-540 MJ/m$^3$ or about 350-520 MJ/m$^3$.

"Elasticity" refers to the property of a body which tends to recover its original size and shape after deformation. Plasticity, deformation without recovery, is the opposite of elasticity. On a molecular configuration of the fiber, recoverable or elastic deformation is possible by stretching (reorientation) of inter-atomic and inter-molecular structural bonds. Conversely, breaking and re-forming of intermolecular bonds into new stabilized positions causes non-recoverable or plastic deformations.

It is understood that the fibers of the invention may be used to form spheres, nanofibrils, hydrogels, threads, foams, films for use in biotechnology, medicine, pharmaceutical and food applications, cosmetics, in electronic devices and for other commercial purposes. More specifically, it may be used for preparing, inter alia, bullet proof vests, automotive and aircraft parts, surface coatings, as well as wound closure systems and wound dressings. Or, in other words, applications, in which no thread structures of spider silk proteins are required.

Another aspect of the invention concerns a scaffold comprising or consisting of the isolated fibrilar structure of the invention.

As mentioned, the polypeptides of the present invention and specifically, fibrilar structures generated therefrom by the method of the invention may be used in the field of reconstructive medicine such as for the generation of scaffolds.

As used herein, the term "scaffold" refers to a 3D matrix. The scaffold may be fully comprised of the polypeptides of the present invention, specifically, the fibrilar structures generated therefrom, or may comprise a solid support on which is layered the compositions of the present invention. A "solid support," as used refers to a three-dimensional matrix or a planar surface (e.g. a cell culture plate) on which cells may be cultured. The solid support can be derived from naturally occurring substances (i.e., protein based) or synthetic substances.

The scaffolds of the present invention may be administered to subjects in need thereof for the regeneration of tissue such as connective tissue, muscle tissue such as cardiac tissue and pancreatic tissue. Examples of connective tissues include, but are not limited to, cartilage (including, elastic, hyaline, and fibro cartilage), collagen, adipose tissue, reticular connective tissue, embryonic connective tissues (including mesenchymal connective tissue and mucous connective tissue), tendons, ligaments, and bone.

The scaffold of the present invention may thus be used for treating a cartilage or bone disease or condition. Exemplary cartilage conditions include, but are not limited to osteoarthritis, limited joint mobility, gout, rheumatoid arthritis, osteoarthritis, chondrolysis, scleroderma, degenerative disc disorder and systemic lupus erythematosus.

The invention further provides a method of preparing a scaffold comprising at least one high molecular ordered fibrilar structure consisting of at least one isolated polypeptide comprising an amino acid sequence of fibrous protein monomer attached to a heterologous polysaccharide binding domain. The method comprises the steps of (a) providing a solution of at least one high molecular ordered fibrilar structures. It should be appreciated that these fibrilar structures are prepared by the method of the invention. The next step (b) involves purring the fibrilar structures solution into a mold; and (c) maintaining the mold under conditions which allow the formation of said scaffold.

According to another particular embodiment, the fiber scaffold may be formed by collecting the obtained fiber(s) or by allowing the obtained fiber(s) to collect. "Collecting" may comprise accumulating the obtained fiber(s), bundling and/or gathering the fiber(s) together, thereby forming a mass of fiber(s) or a fiber scaffold. Alternatively, the fiber(s) may be allowed to accumulate, bundle and/or gather together to form a mass of fiber or fiber scaffold. The collection of the deposited thin film or fiber(s) may be modified to obtain structures such as assemblies consisting of aligned fibers. Even more in particular, the obtained fiber(s) may be collected or allowed to collect against a wall, barrier, mesh and/or filter.

Due to its high strength, elasticity and low weight of the invention's resulting material, it may have numerous utilities in medicine, in reconstruction of tissues, as scaffolds for growth of cells, as support for bone, ligaments and tendon, and as parts of implantable medical devices, etc.

Thus, another aspect of the invention relates to a pharmaceutical composition comprising as an active ingredient the high molecular ordered fibrilar structure of the invention. Said pharmaceutical composition may be used for the treatment of various diseases and conditions, such as, but not limited to, cartilage diseases, osteoarthritis, limited joint mobility, gout, rheumatoid arthritis, osteoarthritis, chondrolysis, scleroderma, degenerative disc disorder and systemic lupus erythematosus.

According to particular embodiments, the composition may be provided in the form of a gel, foam, or a coating used to coat stents and implants, or in forms useful for tissue engineering purposes, in particular for engineering of tissues from mesenchymal origin. In other embodiments, the composition of the invention is a pharmaceutical composition.

As used herein, the term "treating" refers to inhibiting or arresting the development of a disease, disorder or condition and/or causing the reduction, remission, or regression of a disease, disorder or condition in an individual suffering from, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

As used herein, the term "subject" refers to mammals, including, but not limited to, humans, canines and horses.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Alternately, one may administer the pharmaceutical composition in a local rather than systemic manner, for example, via injection of the pharmaceutical composition directly into a tissue region of a patient. Thus, for treatment of urinary incontinence, the compositions of the present invention may be administered directly to the area surrounding the urethra. For treatment of cartilage diseases, the compositions of the present invention may be administered by intra-articular administration via a joint (e.g. directly into the knee, elbow, hip, sternoclavicular, temporomandibular, carpal, tarsal, wrist, ankle, intervertebral disk or a ligamentum flavum. For disc replacement, the pharmaceutical compositions of the present invention may also be administered directly into the pulposus.

According to a particular embodiment of this aspect of the present invention, the compositions of the present invention may be administered directly into the discs for total disc replacement, total disc nucleus pulposus replacement or disc nucleus polposus augmentation and repair or directly into the breast for breast augmentation. According to this embodiment, the compositions may be comprised in injectable non-crosslinked formulations. Following injections of such formulations, photopolymerization may be initiated in situ. This may be affected using classical crosslinking techniques including gluteraldehyde, or crosslinking via sugar molecules.

Pharmaceutical compositions of the present invention may be manufactured by processes well known in the art, e.g., by means of conventional mixing, dissolving, granulating, dragee-making, levitating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulator agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogenes-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (composition) effective to prevent, alleviate or ameliorate symptoms of a disorder (e.g. cartilage or bone disease).

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

In yet further embodiments, the composition of the invention may be a cosmetic composition.

Thus, according to one embodiment, the invention provides a cosmetic composition comprising the isolated high molecular ordered fibrilar structure of the invention. Said cosmetic composition may be used, e.g., as scaffolds, or for cosmetic-restoration of a damaged body tissue.

The term "cosmetic composition" relates to a composition having beneficial skin or other superficial tissue esthetic properties, such as improving or enhancing skin tone and color, hair color and shine, hiding superficial tissue imperfections such as blemishes and scars, or preventing future or cumulative damage such as sunlight damage and skin aging.

Dermatological or cosmetic compositions for the treatment according to the invention are applied topically on the epidermis as ointment pomades, lotions, creams and gels, and on mucous membranes as water emulsions such as creams, lotions or gels. The cosmetic products the may be produced using such a composition include products such as shaving cream, hand cream, shampoo, soap, conditioner, body cream, sun skin-protection, face cream, or body lotion. The ratio of components in the cosmetic composition according to this invention can be adjusted according to the intended application of the cosmetic composition. As mentioned, the compositions of the present invention may also be used as cosmetic agents for treatment of skin and hair.

As already explained above, the fibrilar structures or threads as defined herein may be used in the field of biotechnology and/or medicine, preferably for the manufacture of wound closure or coverage systems, suture materials for use in neurosurgery or ophthalmic surgery. Furthermore, the proteins/threads may preferably be used for the manufacture of replacement materials, preferably artificial cartilage or tendon materials.

Thus, an additional aspect of the invention relates to an article comprising at least one isolated high molecular ordered fibrilar structure of the invention. The term "article" or "an article of manufacture" includes manufactured items which are tangible, movable and independent objects. More specifically, herein the term "article" refers to such manufactured items which comprise or incorporate at least one of the fibrilar structures of the invention and specifically, the fiber of the invention. Non-limiting example of such articles include: synthetic spider-silk coated stents and sutures, dermal patches, tissue scaffold material, fabrics, vests, bullet-proof vests, ropes, threads, cosmetics, etc.

Examples of such articles are threads used for surgical sutures, or threads used for weaving garments or the articles may be scaffolds used for various tissue engineering aspects. Other examples of articles according to the invention include medical devices such as medical adhesive strips, skin grafts, replacement ligaments, and surgical mesh, wound closure or coverage systems, suture materials, replacement materials, preferably artificial cartilage, tendon materials, implants and catheters and in a wide range of industrial and commercial products, such as clothing fabric, bullet-proof vest lining, container fabric, bag or purse straps, cable, rope, fishing line, adhesive binding material, non-adhesive binding material, strapping material, automotive covers and parts, aircraft construction material, weatherproofing material, flexible partition material, sports equipment; and, in fact, in nearly any use of fiber or fabric for which high tensile strength and elasticity are desired characteristics. Adaptability and use of the stable fiber product in other forms, such as a dry spray coating, bead-like particles, or use in a mixture with other compositions is also contemplated by the present invention.

In addition the fiber and the fibrilar structure of the invention may be used for non-medical purposes for example in the military and avian industry where high strength and low weight are important. Specific embodiment of the invention contemplates the use of the fibrilar structures, specifically fibers of the invention for the manufacture of high-strength and low-weight artifacts, for military use, such as in aviation, armory or amour.

In another embodiment, the fibrilar structures or any compositions thereof according to the present invention may be used to coat a metallic stent. Because the fibrilar structures may be made flexible, they will expand with the stent without ripping, while the stiffness of the metal stent will prevent the fibrilar structures from elastically assuming its previous shape. The fibrilar structures or any compositions thereof being highly bioavailable may release heparin or other anti-coagulants or anti-inflammatory agents to prevent the formation of clots or scar tissue, which could close off the blood vessel or throw off a thrombus that could cause circulatory problems, including stroke, elsewhere in the body. Alternatively or in addition, angiogenic agents may be used to promote the remodeling of the blood vessel surrounding the stent. Indeed, any biomolecule, small molecule, or bioactive agent may be combined with the compositions of the present invention. Such molecules may be covalently or non-covalently linked with the compositions.

The articles or any compositions thereof according to the present invention may also be used to prepare "long term" medical devices. Unlike typical permanent medical devices, the compositions of the present invention will degade over time. For example, the material may be fabricated into a biodegradable cardiac stent. Preferably, the compositions are combined with a harder polymer that plastically forms for the production of stents. Exemplary polymers include any of the polymers listed above, preferably biodegradable polymers. The bio-rubber acts as a plasticizer that enables the stent to expand into the desired shape after implantation. The stent increases the diameter of the blood vessel to allow easier circulation, but, because the stent is biodegradable, surrounding blood vessels increase in diameter without thrombosis or covering the stent with scar tissue, which would reclose the blood vessel. The time the stent should remain in place and retain its shape before degradation will vary from patient to patient and depend partially on the amount of blockage and the age of the patient (e.g., older patients require more time to heal). One skilled in the art will easily be able to adjust the molecular weight and cross-link density of the compositions in the stent to adjust the degradation rate. As for the coated stent, the degradable stent may release biomolecules, small molecules, bioactive agents, or some combination of these in situ.

The articles or any compositions thereof according to the present invention may also be used to support in vivo sensors and catheters. The articles may be constructed into a chamber for an optical fiber-based sensor or a coating for a catheter that is inserted into the area of interest. In a sensor, the chamber contains a specific chromophore-bonded receptor for the molecule of interest. When an analyte attaches to the receptor, the chromophore will either emit or absorb light at an specific wavelength. The absorption or emission may be detected by an apparatus connected to the optical fiber. The sensor may be used for short term, continuous monitoring, for example, for ten to fifteen days. Likewise, a catheter may be used to periodically deliver drugs or other small molecules or bioactive agents to a specific site or intravenously. Use of biodegradable articles of the present invention reduces the formation of scar tissue which would ordinarily form around a shunt or other implant that is used for more than two weeks. The degradation rate of the composition should be optimized so that there is not significant degradation of the material while it is in place in the patient.

The articles or any compositions thereof according to the present invention may also be used for other wounds that are hard to close or that fail to heal properly through normal physiologic mechanisms. For example, diabetics often get skin injuries ("diabetic ulcers"), especially in the lower extremities, which take a long time to heal or fail to heal properly due to poor circulation. The use of the present articles to deliver antibiotics or anti-inflammatory agents to these wounds will aid healing and provide a cover for the wound.

Other implantable medical devices which may be fabricated from the articles of the present invention include artificial blood vessels, catheters and other devices for the removal or delivery of fluids to patients, artificial hearts, artificial kidneys, orthopedic pins, plates and implants; catheters and other tubes (including urological and biliary tubes, endotracheal tubes, peripherably insertable central venous catheters, dialysis catheters, long term tunneled central venous catheters peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses (including breast implants, penile prostheses, vascular grafting prostheses, aneurysm repair devices, heart valves, artificial joints, artificial larynxes, otological implants), anastomotic devices, vascular catheter ports, clamps, embolic devices, wound drain tubes, hydrocephalus shunts, pacemakers and implantable defibrillators, and the like.

All scientific and technical terms used herein have meanings commonly used in the art unless otherwise specified. The definitions provided herein are to facilitate understanding of certain terms used frequently herein and are not meant to limit the scope of the present disclosure.

As used herein the term "about" refers to ±10% The terms "comprises", "comprising", "includes", "including", "having" and their conjugates mean "including but not limited to". The term "consisting of means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range.

As used herein the term "about" refers to ±10%. The terms "comprises", "comprising", "includes", "including", "having" and their conjugates mean "including but not limited to". This term encompasses the terms "consisting of" and "consisting essentially of". The phrase "consisting essentially of" means that the composition or method may include additional ingredients and/or steps, but only if the additional ingredients and/or steps do not materially alter the basic and novel characteristics of the claimed composition or method. Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

It should be noted that various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Reference is now made to the following examples, which together with the above descriptions, illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley; Sons, New York (1988); Watson et al., "Recombinant DNA", Scientific American. Books, New York; Birren et al. (eds) "Genome Analysis: A Laboratory Manual Series", Vols. 1-4, Cold Spring Harbor Laboratory Press, New York (1998). "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. L, ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Experimental Procedures

Construction of Silk-CBD Fusion Gene

The 15mer-spider silk is a synthetic gene optimized for expression in *E. coli*. The gene was provided by Prof. David Kaplan at The Departments of Chemical and Biological Engineering, Biomedical Engineering and Chemistry, Tufts University, Medford, Mass., USA. The synthetic 15mer silk gene is a design of 15 repeats of a monomer consensus derived from the native sequence of the spidroin 1 sequence of *Nephila clavipes* (Accession No. PI9837, as also denoted by SEQ ID NO: 1 (nucleic acid sequence), SEQ ID NO: 2 (amino acid sequence) and FIG. 1).

As shown by FIG. 3, the 15mer synthetic gene was provided in a pET30a vector, which contains an N and C terminal His tag (6H in FIG. 3) enabling purification of the protein on Ni-NTA column.

The 15mer gene was cloned into the NcoI-NotI restriction sites of the pET30a MCS.

Construction of 15mer-CBD Fusion Gene for Expression in *E. Coli*

*Clostridium cellulovorans* CBD (CBDclos, Accession No. M73817.1, as denoted by SEQ ID NO: 3 (nucleic acid sequence) and SEQ ID NO: 4 (amino acid sequence) and FIG. 2) was fused to the 3' end of the 15mer spider silk synthetic gene. The fusion gene is referred to as 15mer-CBD.

PCR reactions on CBDclos were used to create the 15mer-CBD fusion.

More specifically, PCR primers were designed in order to construct the fusion gene mentioned above (Table 1 below). The PCR primers add an N-terminal SpeI and a C-terminal XhoI restriction sites to the CBDclos gene template.

TABLE 1

| Primer name | Sequence | description | Tm ° C. |
|---|---|---|---|
| 1 CBDSpeI_for | GACTAGTATGGCAGCGACA TCATCAATGTC (also denoted by SEQ ID NO. 7) | Forward primer of CBD160 + SpeI site | 56 |
| 2 CBDSXhoI_rev | CTCGAGATCAAATGTTGCA GAAGTAGGATTAATTATTG (also denoted by SEQ ID NO. 8) | Reverse primer of CBD160 + XhoI site | 56 |

CBDclos gene served as a PCR template for the cloning of the fusion gene. The PCR was performed according to the reaction mentioned in Table 2 below. ExTaq™ (Takata, Madison Wis.) is a proof reading enzyme suitable for TA cloning.

TABLE 2

| Ingredient | Volume (µl) |
|---|---|
| TaKaRa ExTaq ™ (5 units/µl) | 0.5 |
| 10× ExTaq Buffer (Mg$^{2+}$ plus) | 5 |
| dNTP Mixture (2.5 mM each) | 4 |
| CBDclos DNA | 1 |
| Primer 1 CBDSpeI_for (10 µmol) | 1 |
| Primer 2 CBDSXhoI_rev (10 µmol) | 1 |
| Sterilized distilled water | Up to 50 |

A standard PCR method was designed for the reaction: 94° C. for 4 min, 35 cycles of 94° C. for 10 sec., 56° C. for 20 sec., 72° C. for 1 min., 72° C. for 4 min.

The DNA product was separated on 1% agarose gel. The 550 base pairs product was excised with a scalpel and the DNA was purified with HiYield™ Gel/PCR DNA extraction kit (RBC Taipei, Taiwan) and cloned into pGEM-T Easy vector (Promega Corporation, Madosim Wis.). The presence of SpeI-CBDclos-XhoI was verified by sequencing. The sequencing was performed using T7 and Sp6 primers that are complimentary to pGEM-T Easy vector. The sequencing results confirmed the cloning of SpeI-CBDclos-XhoI into the pGEM-T vector.

*Cloning of SpeI-CBDclos-XhoI into pET30a-15mer

As shown by FIG. 4, the pGEM-T-SpeI-CBDclos-XhoI and pET30a-15mer vectors were digested with SpeI and XhoI restriction enzymes. SpeI-CBDclos-XhoI was cloned into pET30a-15mer vector. Positive 15mer-CBD clones were selected by PCR with primers 1 and 2 mentioned above (SEQ ID NO. 7 and 8, Table 1) and subjected to further restriction analysis. The presence of CBDclos in the pET30a-15mer was also verified by sequencing. The sequencing was performed using T7 promoter and terminator primers that are complimentary to pET30a vector. The nucleic acid and the amino acid sequence are denoted by SEQ ID NO: 5 and SEQ ID NO: 6, respectively, and also disclosed by FIG. 5.

Expression and Purification of Silk and Silk-CBD Fusion Protein

*Expression of 15mer and 15mer-CBDclos Proteins in *E. Coli*

The pET30a-15mer and pET30a-15mer-CBDclos vectors were transformed into BL21(DE3) (Novagen, EMD Chemicals, Inc. CA). 5 ml of overnight cultures were grown in LB medium with 50 mg/l kanamicin at 37° C. rotary shaker. These starters were used for inoculation of 250 to 350 ml of LB with 50 mg/l kanamicin at a ratio of 1/100 of starter to culture volume. At O.D.600 of 0.6 to 0.9 expression was induced with 1 mM IPTG. Following 4 hours from induction, bacteria were harvested by centrifugation. 1 pellet was divided to 50 ml aliquots for initial analysis and the pellets were stored at −80° C.

*FPLC Purification of 6H-15mer and 6H-15mer-CBD

Bacterial pellet of 300 ml was re-suspended in 5 ml of 100 mM Tris pH 7.5, 0.1% Triton® X-100, Complete™ (Roche, Basel Switzerland). Bacteria were lyzed by sonication with pulsed bursts for 5 min. on ice bath. The soluble and bacterial precipitates were separated by centrifugation at 15000 RPM for 10 min. at 4° C. The soluble fraction of the proteins was filtered with a syringe filter of 0.45 μm for the purpose of FPLC (GE, Uppsala Sweden) purification on HisTrap™ HP (GE, Uppsala Sweden) Ni-NTA 5 ml column pre-equilibrated according to the user manual.

The purification program was run as follows:
1. 2 column volumes (CV) of binding buffer at 5 ml/min
2. 20-30 ml injection of the lysate at 5 ml/min.
3. 10 CV wash with binding buffer containing 65 mM imidazole.
4. linear gradient up to 500 mM imidazole for 30 min at 5 ml/min with the elution buffer
5. Equilibration with 10 CV of binding buffer at 5 ml/min.
   Binding buffer; 20 mM $NaHPO_4$, 0.5M NaCl, 10 mM imidazole
   Elution buffer; 20 mM $NaHPO_4$, 0.5M NaCl, 0.5M imidazole Eluted proteins were detected at O.D.280. 5 ml fractions were collected and 30 μl of samples boiled with SAB were loaded on a 10% SDS-PAGE gel.

Production of Spider Silk Composite Sponges

The purified 15mer/15mer-CBD protein was dialyzed against water (dialysis ratio of 1:100) for 18 hours, changing the water for 4 times (FIG. 6). After dialysis the protein aqueous solution was concentrated to 6 wt %, and exposed to a sonication treatment. The sonicated concentrate was purred into a Teflon mold. The mold is placed in room temperature for 1 hour and then at −20° C. The protein frozen solution is freeze dried to generate a sponge.

Example 1

Expression and Purification of Dragline Silk and Dragline Silk-CBDclos Proteins

Expression of Dragline Silk and Dragline Silk-CBDclos Proteins in *E. Coli*.

In order to use CBD's ability to form dimers and higher molecular weight compounds for dragline silk proteins' assembly, a fusion silk-CBD protein was produced.

SDS-PAGE analysis of soluble and insoluble fractions of *E. coli* expressing silk proteins presented by FIG. 7, shows that large amounts of silk protein products are found in the soluble fraction, whereas large amounts of silk-CBD protein products are found in the insoluble inclusion bodies fraction.

FPLC purification of 6HIS-dragline silk and 6H-dragline silk-CBD was performed by using Ni-NTA column (FIG. 8), and the purified proteins were analyzed by SDS-PAGE (FIG. 9A) and Western blot analysis with anti-HIS antibodies (FIG. 9B). The results clearly show that large amounts of silk proteins is produced in *E. coli*, and readily purified therefrom.

Example 2

The Effect of Sonication on Dragline-Silk and Dragline Silk-CBD Proteins, FPLC Gel Filtration Gel filtration chromatography separates proteins on the basis of size. Both molecular weight and three-dimensional shape contribute to the degree of retention in the column. In the following experiment the inventors uses two kinds of samples: before and after sonication.

As shown by FIG. 10, in the case of silk proteins (FIG. 10A and FIG. 10C), the sonicated and non-sonicated proteins exited the column at the same time, after 12.73/12.83 ml, respectively, which according to the molecular size markers, correlates to 140 kDa. This means that sonication treatment of silk proteins does not have any effect thereon.

However, in the case of silk-CBD proteins (FIG. 10B and FIG. 10D) there is a clear difference between the samples before and after sonication. Before sonication two major peaks were formed, the first peak exits the column in the void volume, which means it contains a high molecular weight compound, and the second peak exits the column after 11.89 ml, which correlate to 230 kDa. As shown by FIG. 10B, after sonication the extent of the first peak is much higher, meaning that the sonication accelerates or motivates formation of the higher molecular weight compounds.

Example 3

Dynamic Light Scattering (DLS) of Dragline Silk and Dragline Silk-CBD Proteins

Formation of high molecular structures in sonicated samples of the silk-CBD fusion protein, prompt the inventors to further characterize these molecules. Thus, in order to determine the size distribution profile of protein particles found in solution, the inventors used DLS. DLS shines a monochromatic light onto a particles solution, and when the light hits a particle in the solution; the wavelength of the incoming light changes, based on the particle size. A summary of the results is presented in Table 3 and Table 4 below.

TABLE 3

|  | Silk | Silk-sonicated | |
| --- | --- | --- | --- |
| Diameter (nm) | 2.78 ± 0.04 | 3.8 ± 0.11 | 825 ± 405 |
| % volume | 100 | 99.9 | 0.1 |

TABLE 4

|  | Silk-CBD | | Silk-CBD-sonicated | |
| --- | --- | --- | --- | --- |
| Diameter (nm) | 55 ± 36 | 259 ± 30 | 96 ± 8 | 2048 ± 691 |
| % volume | 32 | 68 | 64 | 36 |

The results show that in the purified Silk solution, sonication does not affect the size of the obtained monomer: 2.78 nm versus 3.8 nm monomer size, before and after sonication, respectively. Only a very minor fraction (about 0.1% of volume) contained particles having a large range diameter. However, in the purified Silk-CBD solution, sonication markedly effects the size distribution. As demonstrated by Table 4, before sonication there is a heterogeneous solution with particles in the diameter range of 55 nm and 260 nm, whereas after sonication there is an extensive increase in the diameter of the particles ranging between 96 to about 2050 nm (a large fraction of the sample, 36%), which correlates to the gel filtration results shown above.

Example 4

Solution X-Ray Scattering of Dragline Silk and Dragline Silk-CBD Proteins

In order to further characterize the high molecular structures formed by the silk-CBD proteins, a Solution X-ray scattering assay was next performed. Supramolecular self-assembled structures are composed of various single or multi-layered shapes. Each layer may have different thickness and mean electron density contrast, with respect to the solvent. In self assembled systems, such as liquid crystals, both form and structure factors may have significant contributions to the measured signal. These factors allow extraction of relevant physical parameters, including electron density distribution, correlation distances, domain sizes, elastic constants and parameters describing intermolecular interactions.

The form and the structure factors, measured by solution X-ray scattering, were derived using the X+ program [Székely et al., Langmuir 26:13110-29 (2010); Ben-Nun et al., J. Appl. Cryst. 43:1522-1531 (2010)]. The X+ is a user-friendly, comprehensive, computationally accelerated software program for the analysis of radially integrated signals of solution X-ray scattering from supramolecular self assembled structures. It can address both the form and structure factors which contributions to the signal. The length scale of the method is in the range of 0.1-100 nm.

Measurements of scattering intensity from Silk or Silk-CBD solutions at room temperature was rerecorded and analyzed. Using the X+ program, the form factor was found to be that of infinitely long rods.

As shown by FIGS. 11A and 11C, in Silk samples, there is a very weak signal with apparently no structurally ordered subunits formed in solution before sonication [FIG. 11A, S. (Silk sample) and S.C. (Silk-concentrated sample) lines] or after sonication [FIG. 11C, S. (Silk sample) and S.C. (Silk-concentrated sample) lines].

In the case of the control CBD samples, there is also very weak signal with apparently no structurally ordered subunits formed in solution [FIG. 11C, CBD and CBD C. (CBD concentrated sample) lines].

However, in the case of Silk-CBD, the correlation peak before sonication [FIG. 11A, S.-CBD line] was fitted to one dimensional domain in the range of 80 nm, in which there are three subunits along the a axis with a radius of 26.4 nm stretches from the center of one subunit to the other, as illustrated also in FIG. 12A.

After concentration of the non-sonicated Silk-CBD sample [FIG. 11A, S.-CBD C. line], the peak gets stronger and the radius from the center of one subunit to the other (on the axis) decreases to 24.6 nm, as illustrated by FIGS. 12B and 12C. These results suggest that following concentration of the purified protein sample, the length from the center of one subunit to the other shortens and more subunits are in correlation with the suggested model.

In the silk-CBD samples after sonication, as presented by FIG. 11B and illustrated in FIG. 12D, the correlation peaks were fitted to a two dimensional oblique phase and the lattice parameters obtained from the fit were a=30.8 nm, b=54.98 nm and γ=83.2°. The peak width indicates that there are three subunits along the "a" axis and three along the "b" axis. After sonication of the concentrated Silk-CBD sample [FIG. 11B, S.-CBD C. line], the distance between the different subunits was measured to be a=32.4 nm, b=45.8 nm and γ=93.4°, as also illustrated by FIGS. 12E and 12F.

These results demonstrate the feasibility of forming super molecular structured fibers by attaching CBD to a fibrous protein such as the spider silk protein.

Example 5

TEM Pictures of Silk-CBD Fibers

Figure 13:
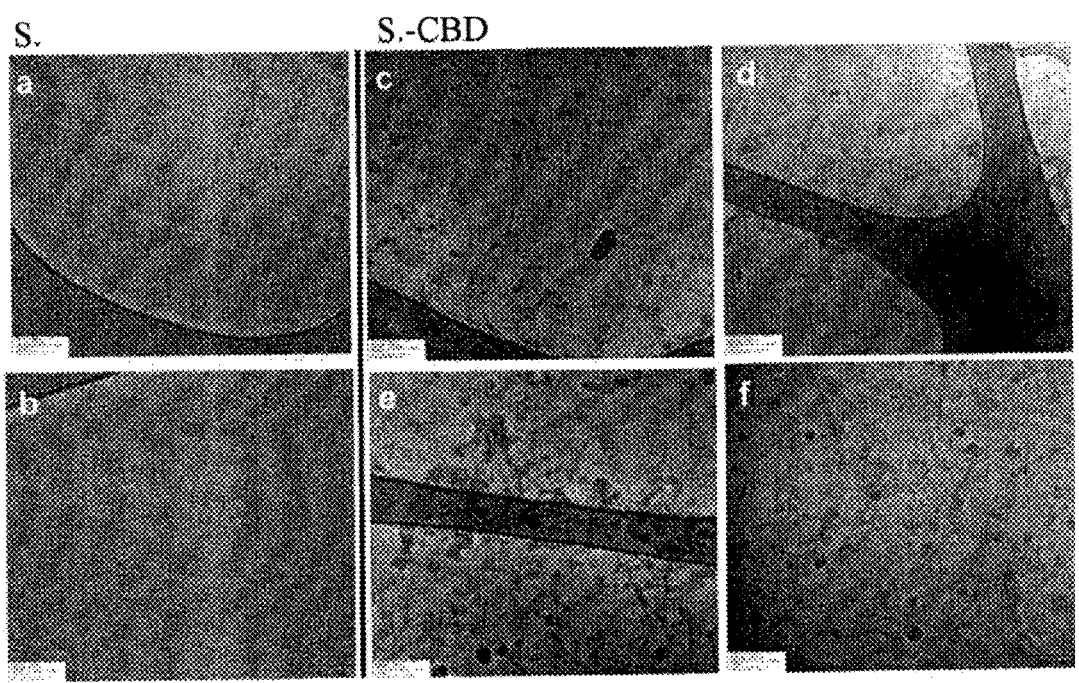

Cryo-TEM 2D images were used to visualize the supramolecular structure of Silk [FIG. 13 (a) and (b)] and Silk-CBD (FIG. 13, c to f) in sonicated solutions. It is evident, from the cryo-TEM images, that Silk doesn't form any high molecular ordered structure in solution, whereas Silk-CBD does form fibers. The length of the Silk-CBD fibers seen in sonicated solutions is in the range of 100-200 nm. The higher order structure detected by DLS cannot be seen in these pictures because only thin layers of sample remain attached to the grid after blotting.

The assembly of Silk-CBD proteins to fibers demonstrates the higher hierarchy ordering when using CBD as a fusion partner that can further dimerize or form higher molecular ordered assemblies.

The invention claimed is:

1. A method for generating high molecular ordered fibrilar structures by directing ordered assembly of fibrous proteins, the method comprising:
   a. providing at least one fibrous protein monomer selected from the group consisting of spider-silk, resilin, elastin, silk-worm silk, collagen and mussel byssus protein;
   b. providing at least one heterologous cellulose binding domain (CBD);
   c. attaching said at least one fibrous protein monomer provided in step (a) to said CBD provided in step (b), thereby obtaining a polypeptide comprising an amino acid sequence of a fibrous protein monomer attached to a heterologous CBD;
   d. providing a solution of the polypeptide obtained in step (c) under conditions which allow folding of said fibrous protein to generate said fibrilar structures;
   e. sonicating the solution of the polypeptide obtained in step (d) under conditions which allow folding of said fibrous protein to generate said fibrilar structures; and
   f. optionally recovering or isolating said fibrilar structures from said solution or liquid medium, thereby obtaining isolated high molecular ordered fibrilar structures.

2. The method according to claim 1, wherein said CBD is CBDclos comprising the amino acid sequence as denoted by SEQ ID NO: 4.

3. The method according to claim 1, wherein said fibrous polypeptide is spider-silk protein.

4. The method according to claim 3, wherein said spider-silk monomer comprises the amino acid sequence as denoted by any one of SEQ ID NO: 2 or SEQ ID NO: 14.

5. The method according to claim 4, wherein said polypeptide comprises the amino acid sequence as denoted by any one of SEQ ID NO: 6 or SEQ ID NO: 16.

6. The method according to claim 5, wherein said fibrilar structure is characterized by at least one of a molecular weight of 230 kDa or higher, a diameter of between about 100 nm to 2100 nm or higher and a length of about 100-200 nm or higher, and wherein said fibrilar structure is arranged in a lattice comprising at least two subunits along an "a" axis and at least two subunits along a "b" axis, and wherein the angle (γ) between at least two adjacent polypeptides is between about 80° to 95° or higher, the distance between at least two subunits along an "a" axis is between about 30 to 35 nm or lower and the distance between at least two subunits along an "b" axis is between about 40 to 55 nm or lower.

* * * * *